(12) United States Patent
Amirana et al.

(10) Patent No.: US 11,559,192 B2
(45) Date of Patent: *Jan. 24, 2023

(54) SYSTEMS AND METHODS FOR VISUALIZING ABLATED TISSUE

(71) Applicants: The George Washington University, Washington, DC (US); 460Medical, Inc., Cambridge, MA (US)

(72) Inventors: Omar Amirana, Cambridge, MA (US); Kenneth C. Armstrong, Cary, NC (US); Matthew W. Kay, Kensington, MD (US); Marco A. Mercader, Arlington, VA (US); Terrance J. Ransbury, Chapel Hill, NC (US); Narine Sarvazyan, Potomac, MD (US)

(73) Assignees: The George Washington University, Washington, DC (US); 460Medical, Inc., Cambridge, MA (US)

( * ) Notice: Subject to any disclaimer, the term of this patent is extended or adjusted under 35 U.S.C. 154(b) by 253 days.

This patent is subject to a terminal disclaimer.

(21) Appl. No.: 16/879,929

(22) Filed: May 21, 2020

(65) Prior Publication Data

US 2020/0352425 A1 Nov. 12, 2020

Related U.S. Application Data

(63) Continuation of application No. 15/986,970, filed on May 23, 2018, now Pat. No. 10,716,462, which is a
(Continued)

(51) Int. Cl.
*A61B 1/04* (2006.01)
*A61B 5/00* (2006.01)
(Continued)

(52) U.S. Cl.
CPC .......... *A61B 1/043* (2013.01); *A61B 1/00009* (2013.01); *A61B 1/00045* (2013.01);
(Continued)

(58) Field of Classification Search
CPC . A61B 1/043; A61B 1/00009; A61B 1/00045; A61B 1/00082; A61B 1/00186;
(Continued)

(56) References Cited

U.S. PATENT DOCUMENTS

| 3,387,305 A | 6/1968 | Shafer |
| 3,831,467 A | 8/1974 | Moore |

(Continued)

FOREIGN PATENT DOCUMENTS

| CN | 1289239 | 3/2001 |
| CN | 1764419 | 4/2006 |

(Continued)

OTHER PUBLICATIONS

Office Action in U.S. Appl. No. 14/952,048 dated Jul. 8, 2020.
(Continued)

*Primary Examiner* — Peter Luong
(74) *Attorney, Agent, or Firm* — Greenberg Traurig, LLP; David J. Dykeman; Roman Fayerberg

(57) ABSTRACT

Systems and methods for visualizing ablated tissue are disclosed. In some embodiments, a system for imaging tissue comprising: a catheter having a distal end and a proximal end; an inflatable balloon disposed about the distal end of the catheter; and an optical housing extending from the distal end of the catheter into the balloon, the optical housing being configured to position inside the balloon a light source for illuminating a tissue outside the balloon and a camera for imaging the illuminated tissue.

20 Claims, 23 Drawing Sheets
(6 of 23 Drawing Sheet(s) Filed in Color)

Related U.S. Application Data continuation of application No. 14/689,475, filed on Apr. 17, 2015, now Pat. No. 10,076,238, which is a continuation-in-part of application No. 13/624,899, filed on Sep. 22, 2012, now Pat. No. 9,014,789, which is a continuation of application No. 13/624,902, filed on Sep. 22, 2012, now Pat. No. 9,084,611.

(60) Provisional application No. 61/537,798, filed on Sep. 22, 2011.

(51) Int. Cl.

| | |
|---|---|
| A61B 5/1459 | (2006.01) |
| A61B 18/00 | (2006.01) |
| A61B 1/00 | (2006.01) |
| A61B 1/06 | (2006.01) |
| A61B 5/145 | (2006.01) |
| A61B 90/35 | (2016.01) |
| A61B 1/05 | (2006.01) |
| A61B 90/30 | (2016.01) |
| A61B 90/00 | (2016.01) |
| A61B 18/14 | (2006.01) |
| A61B 34/30 | (2016.01) |
| A61B 18/02 | (2006.01) |

(52) U.S. Cl.
CPC ...... *A61B 1/00082* (2013.01); *A61B 1/00186* (2013.01); *A61B 1/05* (2013.01); *A61B 1/0638* (2013.01); *A61B 1/0676* (2013.01); *A61B 1/0684* (2013.01); *A61B 5/004* (2013.01); *A61B 5/0044* (2013.01); *A61B 5/0084* (2013.01); *A61B 5/1459* (2013.01); *A61B 5/14503* (2013.01); *A61B 5/14546* (2013.01); *A61B 5/6853* (2013.01); *A61B 18/00* (2013.01); *A61B 18/1492* (2013.01); *A61B 90/30* (2016.02); *A61B 90/35* (2016.02); *A61B 90/361* (2016.02); *A61B 2018/0022* (2013.01); *A61B 2018/0212* (2013.01); *A61B 2034/301* (2016.02); *A61B 2090/365* (2016.02); *Y02A 90/10* (2018.01)

(58) Field of Classification Search
CPC ....... A61B 1/05; A61B 1/0638; A61B 1/0676; A61B 1/0684; A61B 5/004; A61B 5/0044; A61B 5/0084; A61B 5/14503; A61B 5/14546; A61B 5/1459; A61B 5/6853; A61B 18/00; A61B 18/1492; A61B 90/30; A61B 90/35; A61B 90/361; A61B 2018/0022; A61B 2018/0212; A61B 2034/301; A61B 2090/365; Y02A 90/10

See application file for complete search history.

(56) References Cited

U.S. PATENT DOCUMENTS

| | | |
|---|---|---|
| 4,024,873 A | 5/1977 | Antoshkiw et al. |
| 4,619,247 A | 10/1986 | Inoue et al. |
| 5,074,306 A | 12/1991 | Green et al. |
| 5,187,572 A | 2/1993 | Nakamura et al. |
| 5,350,375 A | 9/1994 | Deckelbaum et al. |
| 5,419,323 A | 5/1995 | Kittrell et al. |
| 5,421,337 A | 6/1995 | Richards-Kortum et al. |
| 5,507,287 A | 4/1996 | Palcic et al. |
| 5,540,681 A | 7/1996 | Strul et al. |
| 5,584,799 A | 12/1996 | Gray |
| 5,590,660 A | 1/1997 | MacAulay et al. |
| 5,657,760 A | 8/1997 | Ying et al. |
| 5,713,364 A | 2/1998 | DeBaryshe et al. |
| 5,749,830 A | 5/1998 | Kaneko et al. |
| 5,833,688 A | 11/1998 | Sieben et al. |
| 5,885,258 A | 3/1999 | Sachdeva et al. |
| 5,904,651 A | 5/1999 | Swanson et al. |
| 5,954,665 A | 9/1999 | Ben Haim |
| 6,064,069 A | 5/2000 | Nakano et al. |
| 6,112,123 A | 8/2000 | Kelleher et al. |
| 6,124,597 A | 9/2000 | Shehada et al. |
| 6,174,291 B1 | 1/2001 | McMahon et al. |
| 6,178,346 B1 | 1/2001 | Amundson et al. |
| 6,197,021 B1 | 3/2001 | Panescu et al. |
| 6,208,886 B1 | 3/2001 | Alfano et al. |
| 6,217,573 B1 | 4/2001 | Webster et al. |
| 6,219,566 B1 | 4/2001 | Weersink et al. |
| 6,251,107 B1 | 6/2001 | Schaer |
| 6,289,236 B1 | 9/2001 | Koenig et al. |
| 6,309,352 B1 | 10/2001 | Oraevsky et al. |
| 6,343,228 B1 | 1/2002 | Qu |
| 6,423,055 B1 | 7/2002 | Farr et al. |
| 6,423,057 B1 | 7/2002 | He et al. |
| 6,450,971 B1 | 9/2002 | Andrus et al. |
| 6,516,217 B1 | 2/2003 | Tsujita |
| 6,522,913 B2 | 2/2003 | Swanson et al. |
| 6,542,767 B1 | 4/2003 | McNichols et al. |
| 6,572,609 B1 | 6/2003 | Farr et al. |
| 6,584,360 B2 | 6/2003 | Francischelli et al. |
| 6,626,900 B1 | 9/2003 | Sinofsky et al. |
| 6,648,883 B2 | 11/2003 | Francischelli et al. |
| 6,658,279 B2 | 12/2003 | Swanson et al. |
| 6,663,622 B1 | 12/2003 | Foley et al. |
| 6,663,627 B2 | 12/2003 | Francischelli et al. |
| 6,671,535 B1 | 12/2003 | McNichols et al. |
| 6,697,657 B1 | 2/2004 | Shehada et al. |
| 6,706,038 B2 | 3/2004 | Francischelli et al. |
| 6,716,196 B2 | 4/2004 | Lesh et al. |
| 6,743,225 B2 | 6/2004 | Sanchez et al. |
| 6,746,401 B2 | 6/2004 | Panescu |
| 6,761,716 B2 | 7/2004 | Kadhiresan et al. |
| 6,825,928 B2 | 11/2004 | Liu et al. |
| 6,936,047 B2 | 8/2005 | Nasab et al. |
| 6,937,885 B1 | 8/2005 | Lewis et al. |
| 6,942,657 B2 | 9/2005 | Sinofsky et al. |
| 6,953,457 B2 | 10/2005 | Farr et al. |
| 6,974,454 B2 | 12/2005 | Hooven |
| 6,975,898 B2 | 12/2005 | Seibel |
| 6,975,899 B2 | 12/2005 | Faupel et al. |
| 6,979,290 B2 | 12/2005 | Mourlas et al. |
| 6,989,010 B2 | 1/2006 | Francischelli et al. |
| 7,001,383 B2 | 2/2006 | Keidar |
| 7,029,470 B2 | 4/2006 | Francischelli et al. |
| 7,047,068 B2 | 5/2006 | Haissaguerre |
| 7,130,672 B2 | 10/2006 | Pewzner et al. |
| 7,192,427 B2 | 3/2007 | Chapelon et al. |
| 7,207,984 B2 | 4/2007 | Farr et al. |
| 7,232,437 B2 | 6/2007 | Berman et al. |
| 7,235,045 B2 | 6/2007 | Wang et al. |
| 7,250,048 B2 | 7/2007 | Francischelli et al. |
| 7,252,664 B2 | 8/2007 | Nasab et al. |
| 7,255,695 B2 | 8/2007 | Falwell et al. |
| 7,289,205 B2 | 10/2007 | Yaroslavsky et al. |
| 7,306,593 B2 | 12/2007 | Keidar et al. |
| 7,338,485 B2 | 3/2008 | Brucker et al. |
| 7,357,796 B2 | 4/2008 | Farr et al. |
| 7,367,944 B2 | 5/2008 | Rosemberg et al. |
| 7,367,972 B2 | 5/2008 | Francischelli et al. |
| 7,497,858 B2 | 3/2009 | Chapelon et al. |
| 7,527,625 B2 | 5/2009 | Knight et al. |
| 7,534,204 B2 | 5/2009 | Starksen et al. |
| 7,539,530 B2 | 5/2009 | Caplan et al. |
| 7,587,236 B2 | 9/2009 | Demos et al. |
| 7,591,816 B2 | 9/2009 | Wang et al. |
| 7,596,404 B2 | 9/2009 | Maier et al. |
| 7,598,088 B2 | 10/2009 | Balas |
| 7,640,046 B2 | 12/2009 | Pastore |
| 7,662,152 B2 | 2/2010 | Sharareh et al. |
| 7,681,579 B2 | 3/2010 | Schwartz |
| 7,727,229 B2 | 6/2010 | He et al. |
| 7,727,231 B2 | 6/2010 | Swanson |
| 7,729,750 B2 | 6/2010 | Tromberg et al. |

(56) References Cited

U.S. PATENT DOCUMENTS

| | | |
|---|---|---|
| 7,766,907 B2 | 8/2010 | Dando et al. |
| 7,776,033 B2 | 8/2010 | Swanson |
| 7,822,460 B2 | 10/2010 | Halperin et al. |
| 7,824,397 B2 | 11/2010 | McAuley |
| 7,824,399 B2 | 11/2010 | Francischelli et al. |
| 7,837,676 B2 | 11/2010 | Sinelnikov et al. |
| 7,846,157 B2 | 12/2010 | Kozel |
| 7,862,561 B2 | 1/2011 | Swanson et al. |
| 7,877,128 B2 | 1/2011 | Schwartz |
| 7,918,850 B2 | 4/2011 | Govari et al. |
| 7,930,016 B1 | 4/2011 | Saadat |
| 7,942,871 B2 | 5/2011 | Thapliyal et al. |
| 7,950,397 B2 | 5/2011 | Thapliyal et al. |
| 7,974,683 B2 | 7/2011 | Balas et al. |
| 7,976,537 B2 | 7/2011 | Lieber et al. |
| 7,979,107 B2 | 7/2011 | Lin et al. |
| 7,992,573 B2 | 8/2011 | Wilson et al. |
| 7,996,078 B2 | 8/2011 | Paul et al. |
| 8,007,433 B2 | 8/2011 | Iketani |
| 8,024,027 B2 | 9/2011 | Freeman et al. |
| 8,025,661 B2 | 9/2011 | Arnold et al. |
| 8,050,746 B2 | 11/2011 | Saadat et al. |
| 8,078,266 B2 | 12/2011 | Saadat et al. |
| 8,123,742 B2 | 2/2012 | Berger |
| 8,123,745 B2 | 2/2012 | Beeckler et al. |
| 8,129,105 B2 | 3/2012 | Zuckerman |
| 8,131,350 B2 | 3/2012 | Saadat et al. |
| 8,137,333 B2 | 3/2012 | Saadat et al. |
| 8,144,966 B2 | 3/2012 | Provenzano et al. |
| 8,146,603 B2 | 4/2012 | Thapliyal et al. |
| 8,147,484 B2 | 4/2012 | Lieber et al. |
| 8,152,795 B2 | 4/2012 | Farr et al. |
| 8,160,680 B2 | 4/2012 | Boyden et al. |
| 8,175,688 B2 | 5/2012 | Lewis et al. |
| 8,180,436 B2 | 5/2012 | Boyden et al. |
| 8,188,446 B2 | 5/2012 | Ohno |
| 8,195,271 B2 | 6/2012 | Rahn |
| 8,203,709 B2 | 6/2012 | Ishii |
| 8,219,183 B2 | 7/2012 | Mashke et al. |
| 8,221,310 B2 | 7/2012 | Saadat et al. |
| 8,235,985 B2 | 8/2012 | Saadat et al. |
| 8,241,272 B2 | 8/2012 | Arnold et al. |
| 8,267,926 B2 | 9/2012 | Paul et al. |
| 8,277,444 B2 | 10/2012 | Arnold et al. |
| 8,298,227 B2 | 10/2012 | Leo et al. |
| 8,309,346 B2 | 11/2012 | Zuckerman |
| 8,317,783 B2 | 11/2012 | Cao et al. |
| 8,333,012 B2 | 12/2012 | Rothe et al. |
| 8,353,907 B2 | 1/2013 | Winkler et al. |
| 8,357,149 B2 | 1/2013 | Govari et al. |
| 8,366,705 B2 | 2/2013 | Arnold et al. |
| 8,369,922 B2 | 2/2013 | Paul et al. |
| 8,374,682 B2 | 2/2013 | Freeman et al. |
| 8,382,750 B2 | 2/2013 | Brannan |
| 8,403,925 B2 | 3/2013 | Miller et al. |
| 8,414,508 B2 | 4/2013 | Thapliyal et al. |
| 8,417,321 B2 | 4/2013 | Saadat et al. |
| 8,417,323 B2 | 4/2013 | Uzunbajakava et al. |
| 8,419,613 B2 | 4/2013 | Saadat et al. |
| 8,435,232 B2 | 5/2013 | Aeby et al. |
| 8,444,639 B2 | 5/2013 | Arnold et al. |
| 8,460,285 B2 | 6/2013 | Wang et al. |
| 8,463,366 B2 | 6/2013 | Freeman et al. |
| 8,500,730 B2 | 8/2013 | Lee et al. |
| 8,504,132 B2 | 8/2013 | Friedman et al. |
| 8,511,317 B2 | 8/2013 | Thapliyal et al. |
| 8,540,704 B2 | 9/2013 | Melsky et al. |
| 8,548,567 B2 | 10/2013 | Maschke et al. |
| 8,556,892 B2 | 10/2013 | Hong et al. |
| 8,583,220 B2 | 11/2013 | Schwartz |
| 8,603,084 B2 | 12/2013 | Fish et al. |
| 8,607,800 B2 | 12/2013 | Thapliyal et al. |
| 8,628,520 B2 | 1/2014 | Sharareh et al. |
| 8,641,705 B2 | 2/2014 | Leo et al. |
| 8,641,706 B2 | 2/2014 | Lieber et al. |
| 8,690,758 B2 | 4/2014 | Matsumoto |
| 8,702,690 B2 | 4/2014 | Paul et al. |
| 8,709,008 B2 | 4/2014 | Willis et al. |
| 8,728,077 B2 | 5/2014 | Paul et al. |
| 8,755,860 B2 | 6/2014 | Paul et al. |
| 8,774,906 B2 | 7/2014 | Harks et al. |
| 8,808,281 B2 | 8/2014 | Emmons et al. |
| 8,849,380 B2 | 9/2014 | Patwardhan |
| 8,858,495 B2 | 10/2014 | Tegg et al. |
| 8,876,817 B2 | 11/2014 | Avitall et al. |
| 8,882,697 B2 | 11/2014 | Celermajer et al. |
| 8,894,589 B2 | 11/2014 | Leo et al. |
| 8,894,641 B2 | 11/2014 | Brannan |
| 8,900,219 B2 | 12/2014 | Sinofsky et al. |
| 8,900,225 B2 | 12/2014 | Bar-Tai et al. |
| 8,900,228 B2 | 12/2014 | Grunewald et al. |
| 8,900,229 B2 | 12/2014 | Govari et al. |
| 8,906,011 B2 | 12/2014 | Gelbart et al. |
| 8,915,878 B2 | 12/2014 | Winkler et al. |
| 8,923,959 B2 | 12/2014 | Boveja et al. |
| 8,926,604 B2 | 1/2015 | Govari et al. |
| 8,929,973 B1 | 1/2015 | Webb et al. |
| 8,948,851 B2 | 2/2015 | Leblond et al. |
| 8,951,247 B2 | 2/2015 | Ding et al. |
| 8,986,292 B2 | 3/2015 | Sliwa et al. |
| 8,986,298 B2 | 3/2015 | Lee et al. |
| 8,998,890 B2 | 4/2015 | Paul et al. |
| 8,998,892 B2 | 4/2015 | Winkler et al. |
| 8,998,893 B2 | 4/2015 | Avitall |
| 9,008,746 B2 | 4/2015 | Pastore et al. |
| 9,014,789 B2 | 4/2015 | Mercader et al. |
| 9,084,611 B2 | 7/2015 | Amirana et al. |
| 9,220,411 B2 | 12/2015 | Hillman |
| 9,233,241 B2 | 1/2016 | Long |
| 9,277,865 B2 | 3/2016 | Yamaguchi et al. |
| 10,076,238 B2 | 9/2018 | Amirana et al. |
| 10,143,517 B2 | 12/2018 | Ransbury et al. |
| 10,568,535 B2 | 2/2020 | Roberts et al. |
| 10,682,179 B2 | 6/2020 | Ransbury et al. |
| 10,716,462 B2 | 7/2020 | Amirana et al. |
| 10,722,301 B2 | 7/2020 | Amirana et al. |
| 10,736,512 B2 | 8/2020 | Mercader et al. |
| 10,779,904 B2 | 9/2020 | Ransbury et al. |
| 11,096,584 B2 | 8/2021 | Mercader et al. |
| 2002/0042556 A1 | 4/2002 | Sugimoto et al. |
| 2002/0123666 A1 | 9/2002 | Matsumoto |
| 2002/0143326 A1 | 10/2002 | Foley et al. |
| 2003/0028188 A1 | 2/2003 | Paddock et al. |
| 2003/0120142 A1 | 6/2003 | Dubuc et al. |
| 2003/0120144 A1 | 6/2003 | Grabek et al. |
| 2003/0208252 A1 | 11/2003 | O' Boyle et al. |
| 2004/0073206 A1 | 4/2004 | Foley et al. |
| 2004/0092806 A1 | 5/2004 | Sagon et al. |
| 2004/0097788 A1 | 5/2004 | Mourlas et al. |
| 2004/0138656 A1 | 7/2004 | Francischelli et al. |
| 2004/0187875 A1 | 9/2004 | He et al. |
| 2004/0215310 A1 | 10/2004 | Amirana |
| 2004/0267326 A1 | 12/2004 | Ocel et al. |
| 2005/0014995 A1 | 1/2005 | Amundson et al. |
| 2005/0043637 A1 | 2/2005 | Caplan et al. |
| 2005/0070987 A1 | 3/2005 | Erickson |
| 2005/0075629 A1 | 4/2005 | Chapelon et al. |
| 2005/0119523 A1 | 6/2005 | Starksen et al. |
| 2005/0119548 A1 | 6/2005 | Lin et al. |
| 2005/0197530 A1 | 9/2005 | Wallace et al. |
| 2005/0197623 A1 | 9/2005 | Leeflang et al. |
| 2005/0215899 A1 | 9/2005 | Trahey et al. |
| 2005/0228452 A1 | 10/2005 | Mourlas et al. |
| 2005/0251125 A1 | 11/2005 | Pless et al. |
| 2005/0283195 A1 | 12/2005 | Pastore et al. |
| 2006/0009756 A1 | 1/2006 | Francischelli et al. |
| 2006/0013454 A1 | 1/2006 | Flewelling et al. |
| 2006/0025760 A1 | 2/2006 | Podhajsky |
| 2006/0089636 A1 | 4/2006 | Christopherson et al. |
| 2006/0122583 A1 | 6/2006 | Pesach et al. |
| 2006/0122587 A1 | 6/2006 | Sharareh |
| 2006/0184048 A1 | 8/2006 | Saadat |
| 2006/0229515 A1 | 10/2006 | Sharareh et al. |
| 2006/0229594 A1 | 12/2006 | Franchichelli et al. |

(56) References Cited

U.S. PATENT DOCUMENTS

| | | |
|---|---|---|
| 2007/0015964 A1 | 1/2007 | Eversull et al. |
| 2007/0016079 A1 | 1/2007 | Freeman et al. |
| 2007/0016130 A1 | 1/2007 | Leeflang et al. |
| 2007/0038126 A1 | 2/2007 | Pyle et al. |
| 2007/0049827 A1 | 3/2007 | Donaldson et al. |
| 2007/0083217 A1 | 4/2007 | Eversull et al. |
| 2007/0167828 A1 | 7/2007 | Saadat |
| 2007/0185479 A1 | 8/2007 | Lau |
| 2007/0225697 A1 | 9/2007 | Shroff et al. |
| 2007/0270717 A1 | 11/2007 | Tang et al. |
| 2007/0270789 A1 | 11/2007 | Berger |
| 2007/0270792 A1 | 11/2007 | Hennemann et al. |
| 2007/0270795 A1 | 11/2007 | Francischelli et al. |
| 2007/0276259 A1 | 11/2007 | Okawa et al. |
| 2007/0287886 A1 | 12/2007 | Saadat |
| 2007/0293724 A1 | 12/2007 | Saadat et al. |
| 2008/0009747 A1 | 1/2008 | Saadat et al. |
| 2008/0015569 A1 | 1/2008 | Saadat et al. |
| 2008/0033241 A1 | 2/2008 | Peh et al. |
| 2008/0058650 A1 | 3/2008 | Saadat et al. |
| 2008/0058785 A1 | 3/2008 | Boyden et al. |
| 2008/0058786 A1 | 3/2008 | Boyden et al. |
| 2008/0097476 A1 | 4/2008 | Peh et al. |
| 2008/0101677 A1 | 5/2008 | Mashke et al. |
| 2008/0103355 A1 | 5/2008 | Boyden et al. |
| 2008/0119694 A1 | 5/2008 | Lee |
| 2008/0154257 A1 | 6/2008 | Sharareh et al. |
| 2008/0172049 A1 | 7/2008 | Bredno et al. |
| 2008/0183036 A1 | 7/2008 | Saadat et al. |
| 2008/0212867 A1 | 9/2008 | Provenzano et al. |
| 2008/0214889 A1 | 9/2008 | Saadat et al. |
| 2008/0221448 A1 | 9/2008 | Khuri-Yakub et al. |
| 2008/0228032 A1 | 9/2008 | Starksen et al. |
| 2008/0228079 A1 | 9/2008 | Donaldson et al. |
| 2008/0243214 A1 | 10/2008 | Koblish |
| 2008/0275300 A1 | 11/2008 | Rothe et al. |
| 2008/0281293 A1 | 11/2008 | Peh et al. |
| 2008/0300589 A1 | 12/2008 | Paul et al. |
| 2009/0012367 A1 | 1/2009 | Chin et al. |
| 2009/0030276 A1 | 1/2009 | Saadat et al. |
| 2009/0030412 A1 | 1/2009 | Willis et al. |
| 2009/0054803 A1 | 2/2009 | Saadat et al. |
| 2009/0062790 A1 | 3/2009 | Malchano et al. |
| 2009/0076373 A1 | 3/2009 | Maschke |
| 2009/0076375 A1 | 3/2009 | Maschke |
| 2009/0082623 A1 | 3/2009 | Rothe et al. |
| 2009/0082660 A1 | 3/2009 | Rahn et al. |
| 2009/0125022 A1 | 5/2009 | Saadat et al. |
| 2009/0131931 A1 | 5/2009 | Lee et al. |
| 2009/0143640 A1 | 6/2009 | Saadat et al. |
| 2009/0203962 A1 | 8/2009 | Miller et al. |
| 2009/0204069 A1 | 8/2009 | Hirszowicz et al. |
| 2009/0221871 A1 | 9/2009 | Peh et al. |
| 2009/0227999 A1 | 9/2009 | Willis et al. |
| 2009/0253991 A1 | 10/2009 | Balas et al. |
| 2009/0275799 A1 | 11/2009 | Saadat et al. |
| 2009/0281541 A1 | 11/2009 | Ibrahim et al. |
| 2009/0292211 A1 | 11/2009 | Lin et al. |
| 2009/0299354 A1 | 12/2009 | Melsky et al. |
| 2009/0299363 A1 | 12/2009 | Saadat et al. |
| 2009/0306643 A1 | 12/2009 | Pappone et al. |
| 2010/0022832 A1 | 1/2010 | Makiyama |
| 2010/0041986 A1 | 2/2010 | Nguyen et al. |
| 2010/0056966 A1 | 3/2010 | Toth |
| 2010/0081127 A1 | 4/2010 | Maier et al. |
| 2010/0081948 A1 | 4/2010 | Pastore et al. |
| 2010/0084563 A1 | 4/2010 | Ohno |
| 2010/0114094 A1 | 5/2010 | Thapliyal et al. |
| 2010/0130836 A1 | 5/2010 | Malchano et al. |
| 2010/0152728 A1 | 6/2010 | Park et al. |
| 2010/0198065 A1 | 8/2010 | Thapliyal et al. |
| 2010/0204544 A1 | 8/2010 | Takei |
| 2010/0204561 A1 | 8/2010 | Saadat |
| 2010/0228247 A1 | 9/2010 | Paul et al. |
| 2010/0241117 A1 | 9/2010 | Paul et al. |
| 2010/0274364 A1 | 10/2010 | Pacanowsky |
| 2010/0312094 A1 | 12/2010 | Guttman et al. |
| 2010/0312096 A1 | 12/2010 | Guttman et al. |
| 2010/0331838 A1 | 12/2010 | Ibrahim et al. |
| 2011/0009793 A1 | 1/2011 | Lucero |
| 2011/0019893 A1 | 1/2011 | Rahn et al. |
| 2011/0029058 A1 | 2/2011 | Swanson |
| 2011/0042580 A1 | 2/2011 | Wilson et al. |
| 2011/0066147 A1 | 3/2011 | He et al. |
| 2011/0071647 A1 | 3/2011 | Mahon |
| 2011/0082450 A1 | 4/2011 | Melsky et al. |
| 2011/0082451 A1 | 4/2011 | Melsky et al. |
| 2011/0082452 A1 | 4/2011 | Melsky et al. |
| 2011/0117025 A1 | 5/2011 | Dacosta et al. |
| 2011/0144524 A1 | 6/2011 | Fish et al. |
| 2011/0224494 A1 | 9/2011 | Piskun et al. |
| 2011/0230903 A1 | 9/2011 | Bertolero |
| 2011/0275932 A1 | 11/2011 | Leblond et al. |
| 2011/0276046 A1 | 11/2011 | Heimbecher et al. |
| 2011/0282250 A1 | 11/2011 | Fung et al. |
| 2011/0313417 A1 | 12/2011 | De La Rama et al. |
| 2012/0023638 A1 | 2/2012 | Leicester |
| 2012/0029504 A1 | 2/2012 | Afonso et al. |
| 2012/0109031 A1 | 5/2012 | Vollbrecht |
| 2012/0123276 A1 | 5/2012 | Govari et al. |
| 2012/0143177 A1 | 6/2012 | Avitall |
| 2012/0150046 A1 | 6/2012 | Watson et al. |
| 2012/0184812 A1 | 7/2012 | Terakawa |
| 2012/0184813 A1 | 7/2012 | Terakawa |
| 2012/0197243 A1 | 8/2012 | Sherman et al. |
| 2012/0215112 A1 | 8/2012 | Lewis et al. |
| 2012/0220999 A1 | 8/2012 | Long |
| 2012/0259263 A1 | 10/2012 | Celermajer et al. |
| 2012/0323237 A1 | 12/2012 | Paul et al. |
| 2012/0326055 A1 | 12/2012 | Wilson et al. |
| 2013/0006116 A1 | 1/2013 | Kim et al. |
| 2013/0030425 A1 | 1/2013 | Stewart et al. |
| 2013/0079645 A1 | 3/2013 | Amirana et al. |
| 2013/0085416 A1 | 4/2013 | Mest |
| 2013/0096593 A1 | 4/2013 | Thapliyal et al. |
| 2013/0096594 A1 | 4/2013 | Thapliyal et al. |
| 2013/0102862 A1 | 4/2013 | Amirana et al. |
| 2013/0107002 A1 | 5/2013 | Kikuchi |
| 2013/0137949 A1 | 5/2013 | Freeman et al. |
| 2013/0150693 A1 | 6/2013 | D'Angelo et al. |
| 2013/0150732 A1 | 6/2013 | Manzke et al. |
| 2013/0158545 A1 | 6/2013 | Govari et al. |
| 2013/0172742 A1 | 7/2013 | Rankin et al. |
| 2013/0172875 A1 | 7/2013 | Govari et al. |
| 2013/0226163 A1 | 8/2013 | Peled et al. |
| 2013/0237841 A1 | 9/2013 | Freeman et al. |
| 2013/0253330 A1 | 9/2013 | Demos |
| 2013/0261455 A1 | 10/2013 | Thapliyal et al. |
| 2013/0267875 A1 | 10/2013 | Thapliyal et al. |
| 2013/0281920 A1 | 10/2013 | Hawkins et al. |
| 2013/0282005 A1 | 10/2013 | Koch et al. |
| 2013/0289358 A1 | 10/2013 | Melsky et al. |
| 2013/0289672 A1 | 10/2013 | Hakomori et al. |
| 2013/0296840 A1 | 11/2013 | Condie et al. |
| 2013/0310680 A1 | 11/2013 | Werahera et al. |
| 2013/0331831 A1 | 12/2013 | Wemeth et al. |
| 2014/0031802 A1 | 1/2014 | Melsky |
| 2014/0058244 A1 | 2/2014 | Krocak |
| 2014/0058246 A1 | 2/2014 | Boveja et al. |
| 2014/0081253 A1 | 3/2014 | Kumar et al. |
| 2014/0088418 A1 | 3/2014 | Radulescu et al. |
| 2014/0107430 A1 | 4/2014 | Deno et al. |
| 2014/0121537 A1 | 5/2014 | Aeby et al. |
| 2014/0121660 A1 | 5/2014 | Hauck |
| 2014/0148703 A1 | 5/2014 | Deladi et al. |
| 2014/0163360 A1 | 6/2014 | Stevens-Wright et al. |
| 2014/0163543 A1 | 6/2014 | Allison et al. |
| 2014/0171806 A1 | 6/2014 | Govari et al. |
| 2014/0171936 A1 | 6/2014 | Govari et al. |
| 2014/0180273 A1 | 6/2014 | Nair |
| 2014/0194867 A1 | 7/2014 | Fish et al. |
| 2014/0194869 A1 | 7/2014 | Leo et al. |
| 2014/0275972 A1 | 9/2014 | George et al. |
| 2014/0276687 A1 | 9/2014 | Goodman et al. |

(56) References Cited

U.S. PATENT DOCUMENTS

| | | |
|---|---|---|
| 2014/0276771 A1 | 9/2014 | Miller et al. |
| 2014/0316280 A1 | 10/2014 | Mueller et al. |
| 2014/0324085 A1 | 10/2014 | Thapliyal et al. |
| 2014/0350547 A1 | 11/2014 | Sharareh et al. |
| 2014/0357956 A1 | 12/2014 | Salahieh et al. |
| 2015/0038824 A1 | 2/2015 | Lupotti |
| 2015/0073245 A1 | 3/2015 | Klimovitch et al. |
| 2015/0099979 A1 | 4/2015 | Caves et al. |
| 2015/0141847 A1 | 5/2015 | Sarvazyan et al. |
| 2015/0164332 A1 | 6/2015 | Mercader et al. |
| 2015/0182279 A1 | 7/2015 | Ashton et al. |
| 2015/0196202 A1 | 7/2015 | Mercader et al. |
| 2015/0327753 A1 | 11/2015 | Amirana et al. |
| 2015/0346100 A1 | 12/2015 | Racowsky et al. |
| 2016/0051321 A1 | 2/2016 | Salahieh et al. |
| 2016/0120599 A1 | 5/2016 | Amirana et al. |
| 2016/0120602 A1 | 5/2016 | Ransbury et al. |
| 2016/0143522 A1 | 5/2016 | Ransbury et al. |
| 2017/0014202 A1 | 1/2017 | Ransbury et al. |
| 2017/0135559 A1 | 5/2017 | Horrisberger et al. |
| 2018/0263476 A1 | 9/2018 | Amirana et al. |
| 2019/0053849 A1 | 2/2019 | Ransbury et al. |
| 2020/0008681 A1 | 1/2020 | Sarvazyan |
| 2020/0352644 A1 | 11/2020 | Ransbury et al. |
| 2020/0352645 A1 | 11/2020 | Amirana et al. |
| 2021/0045834 A1 | 2/2021 | Ransbury et al. |
| 2021/0205017 A1 | 7/2021 | Amirana et al. |
| 2021/0369118 A1 | 12/2021 | Sarvazyan |
| 2022/0031377 A1 | 2/2022 | Ransbury et al. |

FOREIGN PATENT DOCUMENTS

| | | |
|---|---|---|
| CN | 101199410 | 6/2008 |
| CN | 102099671 | 6/2011 |
| CN | 102397104 | 4/2012 |
| CN | 203525125 | 4/2014 |
| CN | 106028914 | 10/2016 |
| DE | 102005021205 | 11/2006 |
| DE | 102011083522 | 3/2013 |
| EP | 2691041 | 2/2014 |
| EP | 2 889 013 | 7/2015 |
| JP | 60182928 | 9/1985 |
| JP | 63-262613 | 10/1988 |
| JP | 10150177 | 6/1998 |
| JP | 2006158546 | 6/2006 |
| JP | 20090148550 A | 7/2009 |
| JP | 2011/212423 | 10/2011 |
| JP | 20130544551 A | 12/2013 |
| JP | 20150128586 A | 7/2015 |
| NL | 2002010 | 10/2009 |
| WO | WO 1997/037622 | 10/1997 |
| WO | WO 1999/013934 | 3/1999 |
| WO | WO 2001/001854 | 1/2001 |
| WO | WO 2001/072214 | 10/2001 |
| WO | WO 2003/092520 | 11/2003 |
| WO | WO 2004/028353 | 4/2004 |
| WO | WO 2006/028824 | 3/2006 |
| WO | 2007041542 A2 | 4/2007 |
| WO | WO 2007/109554 | 9/2007 |
| WO | WO 2007/127228 | 11/2007 |
| WO | WO 2008/028149 | 3/2008 |
| WO | WO 2008/114748 | 9/2008 |
| WO | WO 2008/154578 | 12/2008 |
| WO | WO 2010/075450 | 7/2010 |
| WO | WO 2011/025640 | 3/2011 |
| WO | WO 2011/113162 | 9/2011 |
| WO | 2012038824 A1 | 3/2012 |
| WO | WO 2012/049621 | 4/2012 |
| WO | WO 2012/067682 | 5/2012 |
| WO | 20120131577 A2 | 10/2012 |
| WO | WO 2013/044182 | 3/2013 |
| WO | WO 2013/068885 | 5/2013 |
| WO | WO 2013/116316 | 8/2013 |
| WO | WO 2013/169340 | 11/2013 |
| WO | WO 2014/028770 | 2/2014 |
| WO | WO 2015/073871 | 5/2015 |
| WO | WO 2015/077474 | 5/2015 |
| WO | WO 2016/073476 | 5/2016 |
| WO | WO 2016/073492 | 5/2016 |
| WO | WO 2016/086160 | 6/2016 |
| WO | WO 2017/015257 | 1/2017 |

OTHER PUBLICATIONS

Office Action in U.S. Appl. No. 14/541,991 dated Oct. 20, 2020.

Anderson et al. "Real-time spectroscopic assessment of thermal damage: implications for radiofrequency ablation". J Gastrointest Surg. 2004; 8: 660-669.

Anderson, J.K., "Time Course of Nicotinamide Adenine Dinucleotide Diaphorase Staining after Renal Radiofrequency Ablation Influences Viability Assessment", Journal of Endourology, vol. 21, Issue 2, Mar. 5, 2007.

Asfour et al, "Signal decomposition of transmembrane voltage-sensitive dye fluorescence using a multiresolution wavelet analysis" IEEE Trans Biomed Eng. 2011; 58: 2083-2093.

Berthier, J.P., et al., "XeCl Laser Action at Medium Fluences on Biological Tissues: Fluorescence Study and Simulation with a Chemical Solution", Journal of Photochemistry and Photobiology B: Biology, vol. 5, Issues 3-4, pp. 495-503, May 1990.

Boersma et al,. "Pulmonary vein isolation by duty-cycled bipolar and unipolar radiofrequency energy with a multielectrode ablation catheter". Heart Rhythm5:1635-1642, 2008.

Bogaards et al., In Vivo Quantification of Fluorescent Molecular Markers in Real-Time: A Review to Evaluate the Performance of Five Existing Methods, Photodiagnosis and Photodynamic Therapy, vol. 4: 170-178 (2007).

Bogaards et al., n Vivo Quantification of Fluorescent Molecular Markers in Real-Time by Ratio Imaging for Diagnostic Screening and Image-Guided Surgery, Lasers in Surgery and Medicing vol. 39: 605-613 (2007).

Buch et al. "Epicardial catheter ablation of atrial fibrillation." Minerva Med. 2009; 100: 151-157.

Cancio et al., "Hyperspectral Imaging: A New Approach to the Diagnosis of Hemorrhagic Shock", The Journal of Trauma, 2006, vol. 60, No. 5: 1087-1095.

Chance et al, "Fluorescence measurements of mitochondrial pyridine nucleotide in aerobiosis and anaerobiosis" Nature. 1959; 184: 931-4.

Coremans et al, "Pretransplantation assessment of renal viability with NADH fluorimetry", Kidney International, vol. 57, (2000), pp. 671-683.

D'Avila A. "Epicardial catheter ablation of ventricular tachycardia." Heart Rhythm. 2008; 5: S73-5.

Demos et al, "Real time assessment of RF cardiac tissue ablation with optical spectroscopy", Opt Express. 2008; 16: 15286-15296.

Dickfeld et al, "Characterization of Radiofrequency Ablation Lesions With Gadolinium-Enhanced Cardiovascular Magnetic Resonance Imaging" J Am Coll Cardiol. 2006; 47: 370-378.

Dukkipati et al, "Visual balloon-guided point-by-point ablation: reliable, reproducible, and persistent pulmonary vein isolation", Circ Arrhythm Electrophysiol. 2010; 3: 266-273.

Dumas et al, "Myocardial electrical impedance as a predictor of the quality of RF-induced linear lesions." Physiol Meas. 2008; 29: 1195-1207.

Dyer, B., et al., Heart, "The Application of Autofluorescence Lifetime Metrology as a Novel Label-free Technique for the Assessment of Cardiac Disease", vol. 11, Issue Supplement 3, pp. 186, Jun. 2014.

Fleming et al, "Real-time monitoring of cardiac redio-frequency ablation lesion formation using an optical coherence tomography forward-imaging catheter", Journal of Biomedical Optics, May/Jun. 2010, vol. 15(3).

Fleming et al, "Toward guidance of epicardial cardiac radiofrequency ablation therapy using optical coherence tomography" J Biomed Opt. 2010; 15: 041510.

Girard et al, "Contrast-enhanced C-arm CT evaluation of radiofrequency ablation lesions in the left ventricle", JACC Cardiovasc Imaging. 2011; 4: 259-268.

(56) References Cited

OTHER PUBLICATIONS

Grimard et al, "Percutaneous epicardial radiofrequency ablation of ventricular arrhythmias after failure of endocardial approach: a 9-year experience" J Cardiovasc Electrophysiol. 2010; 21: 56-61.
Henz et al, "Simultaneous epicardial and endocardial substrate mapping and radiofrequency catheter ablation as first-line treatment for ventricular tachycardia and frequent ICD shocks in chronic chagasic cardiomyopathy" J Interv Card Electrophysiol. 2009; 26: 195-205.
Himel et al, "Translesion stimulus-excitation delay indicates quality of linear lesions produced by radiofrequency ablation in rabbit hearts", Physiol Meas. 2007; 28: 611-623.
Kalman, J.M., et al., "Cardiac Magnetic Resonance Imaging to Detect Non-Contiguous Scar Following Atrial Fibrillation Ablation: Identifying our Knowledge Gaps", European Heart Journal, Editorial, pp. 1-3, Feb. 26, 2014.
Kay et al, "Locations of ectopic beats coincide with spatial gradients of NADH in a regional model of low-flow reperfusion", Am J Physiol Heart Circ Physiol. 2008; 294: H2400-5.
Khoury et al., "Localizing and Quantifying Ablation Lesions in the Left Ventricle by Myocardial Contrast Echocardiography", J Cardiovasc Electrophysiol. 2004; 15: 1078-1087.
Kim et al, "Materials for multifunctional balloon catheters with capabilities in cardiac electrophysiological mapping and ablation therapy", Nat Mater. 2011; 10: 316-323.
Kistler, P.M., et al., "The Impact of CT Image Integration into an Electroanatomic Mapping System on Clinical Outcomes of Catheter Ablation of Atrial Fibrillation", Journal of Cardiovascular Electyrophysiology, vol. 17, Issue 10, pp. 1093-1101, Oct. 2006.
Lardo, et al "Visualization and temporal/spatial characterization of cardiac radiofrequency ablation lesions using magnetic resonance imaging", Circulation. 2000; 102: 698-705.
Li, "Multiphoton Microscopy of Live Tissues with Ultraviolet Autofluorescence", IEEE Journal of Selected Topic in Quantam Electronics , May/Jun. 2010, vol. 16, Issue 3, pp. 516-513.
Lo et al, "Three-dimensional electroanatomic mapping systems in catheter ablation of atrial fibrillation", Circ J. 2010; 74: 18-23.
Malchano, Z.J., "Integration of Cardiac CT/MR Imaging with Three-Dimensional Electroanatomical Mapping to Guide Catheter Manipulation in the Left Atrium: Implications for Catheter Ablation of Atrial Fibrillation", Journal of Cardiovascular Electrophysiology, vol. 17, Issue 11, pp. 1221-1229, Nov. 2006.
Mayevsky et al. "Oxidation-reduction states of NADH in vivo: from animals to clinical use", Mitochondrion. 2007; 7: 330-339.
Melby et al, "Atrial fibrillation propagates through gaps in ablation lines: implications for ablative treatment of atrial fibrillation", Heart Rhythm. 2008; 5: 1296-1301.
Menes et al, "Laparoscopy: searching for the proper insufflation gas" Surg Endosc. 2000; 14: 1050-1056.
Meng et al "A comparative study of fibroid ablation rates using radio frequency or high-intensity focused ultrasound", Cardiovasc Intervent Radiol. 2010; 33: 794-799.
Mercader et al, "NADH as an Endogenous Marker of Cardiac Tissue Injury at the Site of Radiofrequency Ablation", The George Washington University, Washington DC, Mar. 18, 2011.
Mercader et al, "Use of endogenous NADH fluorescence for real-time in situ visualization of epicardial radiofrequency ablation lesions and gaps", Am J Physiol Heart Circ Physiol, May 2012; 302(10): H2131-H2138.
Naito, H., et al., "Use of Nadh Fluorescence Imaging for Early Detection of Energy Failure and a Prediction of Infarction", Critical Care Medicine, vol. 39, Issue 12, pp. 40, Dec. 2011.
Nath et al, "Basic aspects of radiofrequency catheter ablation", J Cardiovasc Electrophysiol. 1994; 5: 863-876.
Niu et al, "An acute experimental model demonstrating 2 different forms of sustained atrial tachyarrhythmias". Circ Arrhythm Electrophysiol. 2009; 2: 384-392.
Perez et al. "Effects of gap geometry on conduction through discontinuous radiofrequency lesions" Circulation. 2006; 113: 1723-1729.
Ranji et al, "Fluorescence spectroscopy and imaging of myocardial apoptosis", Journal of Biomedical Optics 11(6), 064036 (Nov./Dec. 2006).
Ranji et al, "Quantifying Acute Myocardial Injury Using Ratiometric Fluorometry", IEEE Trans Biomed Eng. May 2009; 56(5): 1556-1563.
Riess et al, "Altered NADH and improved function by anesthetic and ischemic preconditioning in guinea pig intact hearts", Am J Physiol Heart Circ Physiol 283; H53-H60, Mar. 14, 2002.
Robertson, J.O., "Quantification of the Functional Consequences of Atrial Fibrillation and Surgical Ablation on the Left Atrium Using Cardiac Magnetic Resonance Imaging", European Journal of Cardio-Thoracic Surgery, vol. 46, Issue 4, pp. 720-728, Oct. 1, 2014.
Roger et al, "American Heart Association Stastics Committee and Stroke Subcommittee. Heart disease and stroke statistics—2011 update; a report from American Heart Association", Circulation 2011; 123: e18-e209.
Sethuraman et al., "Spectroscopic Intravascular Photoacoustic Imaging to Differentiate Atherosclerotic Plaques", Optics Express, vol. 16, No. 5, pp. 3362-3367, Mar. 3, 2008.
Smith, S., et al., "Imaging Appearances Following Thermal Ablation", Clinical Radiology, vol. 63, Issue 1, pp. 1-11, Jan. 2008.
Sosa et al, "Epicardial mapping and ablation techniques to control ventricular tachycardia". J Cardiovasc Electrophysiol. 2005; 16: 449-452.
Sra, J., et al., "Computed Tomography—Fluoroscopy Image Integration-Guided Catheter Ablation of Atrial Fibrillation", Journal of Cardiovascular Electrophysiology, vol. 18, Issue 4, pp. 409-414, Apr. 2007.
Swartling et al, "Changes in tissue optical properties due to radiofrequency ablation of myocardium", Med Biol Eng Comput. 2003; 41: 403-409.
Swift et al, "Controlled regional hypoperfusion in Langendorff heart preparations". Physiol Meas. 2008; 29: 269-79.
Swift, L.M., et al., "Properties of Blebbistatin for Cardiac Optical Mapping and Other Imaging Applications", European Journal of Physiology, vol. 464, Issue 5, pp. 503-512, Nov. 2012.
Swift, Luther Mitchell, "Real-Time Visualization of Cardiac Ablation Lesions Using Endogenous NADH Fluorescence and Reflected Light", A dissertation submitted to The Faculty of The Columbian College of Arts and Sciences of The George Washington University in partial fulfillment of the requirements for the degree of Doctor of Philosophy, Jul. 23, 2013.
Van Haesendonck C, Sinnaeve A, Willems R, Vandenbulcke F, Stroobandt R, . "Biophysical and electrical aspects of radiofrequency catheter ablation". Acta Cardiol 50: 105-115, 1995.
Vetterlein et al, "Extent of damage in aschemic, nomeperfused myocardium of anesthetized rats", Am J Physiol Heart Circ Physiol 285: H755-H765, 2003.
Vo-Dinh et al., "A Hyperspectral Imaging System for In Vivo Optical Diagnostics", IEEE Engineering in Medicine and Biology Magazine, pp. 40-49, Sep./Oct. 2004.
Weight, C.J., et al., "Correlation of Radiographic Imaging and Histopathology Following Cryoablation and Radio Frequency Ablation for Renal Tumors", The Journal of Urology, vol. 179, Issue 4, pp. 1277-1283, Apr. 2008.
Wu, H., et al., "Real-Time Monitoring of Radiofrequency Ablation and Postablation Assessment: Accuracy of Contrast-Enhanced US in Experimental Rat Liver Model", Radiology, vol. 270, No. 1, pp. 107-116, Jan. 2014.
Yokoyama et al, "Novel contact force sensor incorporated in irrigated radiofrequency ablation catheter predicts lesion size and incidence of steam pop and thrombus", Circ Arrhythm Electrophysiol. 2008; 1: 354-362.
Zuzak et al., "Characterization of a Near-Infrared Laparoscopic Hyperspectral Imaging System for Minimally Invasive Surgery", Analytical Chemistry, vol. 79, No. 12, pp. 4709-4715, Jun. 15, 2007.
International Search Report based on PCT/US2012/056771 dated Dec. 3, 2012.
Office Action in U.S. Appl. No. 13/624,899 dated Oct. 2, 2014.
Office Action in U.S. Appl. No. 13/624,902 dated Oct. 2, 2014.
International Search Report dated Feb. 12, 2015 for PCT/US2014/066660.

(56) References Cited

OTHER PUBLICATIONS

European Search Report completed May 26, 2015 for EP 12 83 4435.
International Search Report dated Feb. 19, 2015 for PCT/US2014/065774.
International SearchReport dated Jan. 19, 2016 for PCT/US2015/058824.
International SearchReport dated Feb. 1, 2016 for PCT/US2015/062732.
International SearchReport dated Feb. 4, 2016 for PCT/US2015/058851.
Office Action in U.S. Appl. No. 14/689,475 dated Apr. 6, 2016.
Office Action in U.S. Appl. No. 14/541,991 dated Jun. 22, 2016.
Office Action in U.S. Appl. No. 14/541,991 dated Feb. 28, 2017.
Office Action in U.S. Appl. No. 14/689,475 dated Apr. 13, 2017.
Office Action in U.S. Appl. No. 14/541,991 dated Jul. 13, 2017.
Office Action in U.S. Appl. No. 14/689,475 dated Aug. 23, 2017.
Office Action in U.S. Appl. No. 14/622,477 dated Oct. 5, 2017.
Office Action in U.S. Appl. No. 14/931,325 dated Mar. 22, 2018.
Office Action in U.S. Appl. No. 14/931,262 dated Apr. 20, 2018.
Office Action in U.S. Appl. No. 14/622,477 dated Jun. 5, 2018.
Office Action in U.S. Appl. No. 14/549,057 dated Jun. 15, 2018.
European Search Report completed Jun. 8, 2018 for EP 15 86 3645.
Office Action in U.S. Appl. No. 14/952,048 dated Aug. 27, 2018.
Office Action in U.S. Appl. No. 14/931,262 dated Aug. 28, 2018.
Office Action in U.S. Appl. No. 14/541,991 dated Sep. 13, 2018.
Office Action in U.S. Appl. No. 15/986,970 dated Sep. 17, 2018.
Office Action in U.S. Appl. No. 14/549,057 dated Dec. 13, 2018.
Office Action in U.S. Appl. No. 14/622,477 dated Dec. 19, 2018.
Office Action in U.S. Appl. No. 15/986,970 dated Jan. 10, 2019.
Office Action in U.S. Appl. No. 14/931,262 dated Jan. 11, 2019.
Office Action in U.S. Appl. No. 16/167,933 dated Jan. 11, 2019.
Office Action in U.S. Appl. No. 14/541,991 dated Jan. 24, 2019.
Office Action in U.S. Appl. No. 14/952,048 dated Mar. 1, 2019.
Office Action in U.S. Appl. No. 14/919,004 dated Apr. 4, 2019.
Office Action in U.S. Appl. No. 14/931,262 dated Aug. 22, 2019.
Office Action in U.S. Appl. No. 14/622,477 dated Sep. 5, 2019.
Office Action in U.S. Appl. No. 15/986,970 dated Sep. 16, 2019.
Office Action in U.S. Appl. No. 16/167,933 dated Sep. 25, 2019.
Extended European Search Report dated Feb. 20, 2019 for EP 16 828 397.6.
Office Action in U.S. Appl. No. 14/952,048 dated Oct. 30, 2019.
Office Action in U.S. Appl. No. 14/919,004 dated Jan. 7, 2020.
Office Action in U.S. Appl. No. 14/541,991 dated Mar. 19, 2020.
International Search Report based on PCT/US2021/012836 dated Apr. 1, 2021.
Office Action in U.S. Appl. No. 14/952,048 dated Jun. 9, 2021.
U.S. Appl. No. 13/624,899, filed Sep. 22, 2012, 2013-0102862, Apr. 25, 2013, U.S. Pat. No. 9,014,789, Apr. 21, 2015, System and Methods for Visualizing Ablate Tissue.
U.S. Appl. No. 13/624,902, filed Sep. 22, 2012, 2013-0079645, Mar. 28, 2013, U.S. Pat. No. 9,084,611, Jul. 21, 2015, System and Methods for Visualizing Ablated Tissue.
U.S. Appl. No. 14/622,477, filed Feb. 13, 2015, 2015-0164332, Jun. 18, 2015, U.S. Pat. No. 10,736,512, Aug. 11, 2020, System and Methods for Visualizing Ablated Tissue.
U.S. Appl. No. 14/689,475, filed Apr. 17, 2015, 2015-0327753, Nov. 19, 2015, U.S. Pat. No. 10,076,238, Sep. 18, 2018, System and Methods for Visualizing Ablated Tissue.
U.S. Appl. No. 15/986,970, filed May 23, 2018, 2018-0263476, Sep. 20, 2018, U.S. Pat. No. 10,716,462, Jul. 21, 2020, System and Methods for Visualizing Ablated Tissue.
U.S. Appl. No. 14/541,991, filed Nov. 14, 2014, 2015-0196202, Jul. 16, 2015, Systems and Methods for Determining Lesion Depth Using Fluorescence Imaging.
U.S. Appl. No. 16/440,778, filed Jun. 13, 2019, 2020-0008681, Jan. 9, 2020, System and Methods for Hyperspectral Analysis of Cardiac Tissue.
U.S. Appl. No. 14/931,262, filed Nov. 3, 2015, 2016-0120599, May 5, 2016, U.S. Pat. No. 10,722,301, Jul. 28, 2020, Systems and Methods for Lesion Assessment.

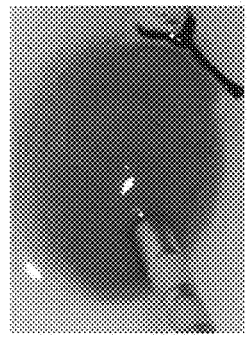
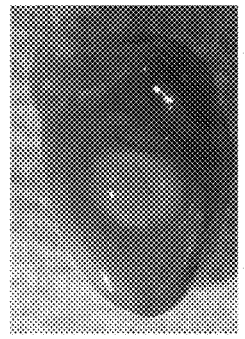
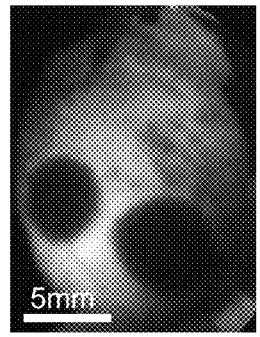
Figure 4A  Figure 4B  Figure 4C
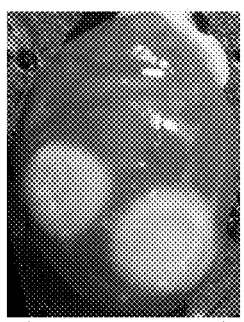
Figure 4D  Figure 4E

*time after ablation*

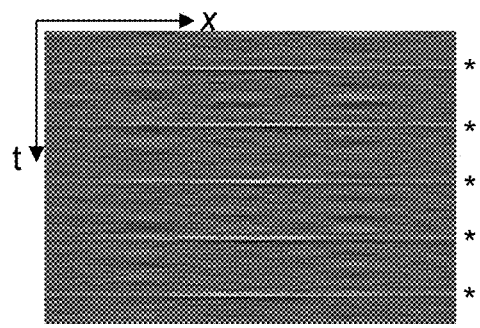
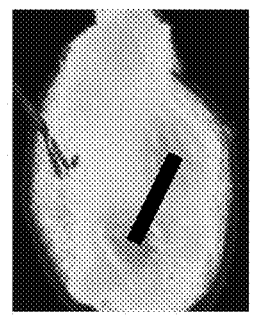
Figure 8A
Figure 8B
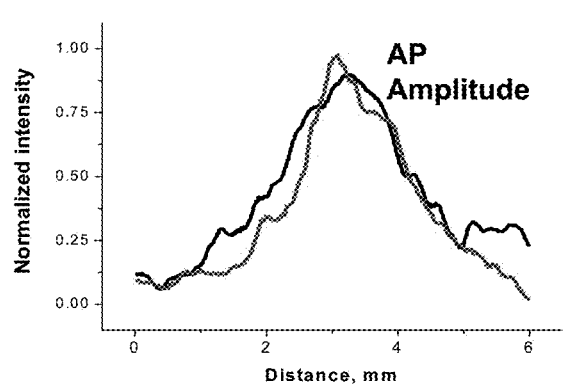
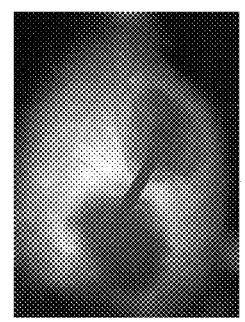
Figure 8C
Figure 8D

Figure 9A     Figure 9B     Figure 9C

*blood on top*

*blood displaced*

SYSTEMS AND METHODS FOR VISUALIZING ABLATED TISSUE

RELATED APPLICATIONS

This application is a continuation application of U.S. application Ser. No. 15/986,970, filed May 23, 2018, which is a continuation application of U.S. application Ser. No. 14/689,475, filed Apr. 17, 2015, now U.S. Pat. No. 10,076,238, which is a continuation of U.S. application Ser. No. 13/624,902, filed Sep. 22, 2012, now U.S. Pat. No. 9,084,611, which is a continuation-in-part of U.S. application Ser. No. 13/624,899, filed on Sep. 22, 2012, now U.S. Pat. No. 9,014,789, and claims the benefit of and priority to U.S. Provisional Application Ser. No. 61/537,798, filed on Sep. 22, 2011, and the entirety of these applications are hereby incorporated herein by reference.

STATEMENT OF GOVERNMENT SUPPORT

This invention was made with Government support under Grant/Contract No. R01 HL095828 awarded by the National Institutes of Health. The Government has certain rights in this invention.

FIELD

The embodiments disclosed herein relate to methods and systems for ablation and visualization of tissue.

BACKGROUND

Exemplary embodiments are directed to techniques used during the treatment of Atrial Fibrillation (AF). Atrial fibrillation is the most common sustained arrhythmia, which currently affects two million Americans. Atrial fibrillation is associated with increased mortality, morbidity and an impaired quality of life, and is an independent risk factor for stroke. The substantial lifetime risk of developing atrial fibrillation underscores the public health burden of the disease, which in the United States alone amounts to an annual treatment cost exceeding $7 billion.

Eighty-five percent of episodes in patients with atrial fibrillation are known to be triggered by focal electrical activity originating from within muscle sleeves that extend into the Pulmonary Veins (PV). Atrial fibrillation may also be triggered by focal activity within the superior vena cava or other atrial structures. These focal triggers can cause atrial tachycardia that is driven by reentrant electrical activity and rotors, which may then fragment into a multitude of electrical wavelets that are characteristic of atrial fibrillation. Prolonged atrial fibrillation can cause functional alterations in membrane ion channels as well as alterations in ion channel expression. These changes further perpetuate atrial fibrillation.

Radiofrequency (RF) ablation is an effective therapy for treating atrial and ventricular rhythm disturbances. Nearly 100,000 RF ablation procedures are performed annually in the United States to treat cardiac arrhythmias. RF ablation targets the key elements of reentrant pathways and/or abnormal ectopic loci without damaging significant amounts of adjacent healthy myocardium and coronary vessels. Ablations are also done with cryo-ablation and laser guided ablation systems.

To perform an RF ablation procedure, a catheter is threaded into the heart and the tip is guided into the atria. A transseptal puncture is made to allow cross-over from the right atrium into the left atrium where the crux of the ablation is performed. The catheter then emits a pulse of high-energy RF electricity that damages atrial tissues and forms scar tissue that blocks abnormal signals. The most common RF ablation treatment of atrial fibrillation consists of placing ablation lesions in a circular fashion around the ostium of each pulmonary vein. The lesions electrically isolate the pulmonary veins to block focal triggers from entering the left atrium. RF lesions can also be placed epicardially during minimally invasive or open heart surgery.

The extent of RF ablation lesions is not simply a function of delivered RF energy, but depends on many factors, including the contact between the catheter tip and the tissue, the thickness of the myocardium, the degree of blood flow, and the presence of fat. Currently we use surrogates to determine anatomy known as 3D mapping systems (CARTO and NAVEX), surrogates can be off by 1 or 2 cm. Current electro-anatomical mapping systems map mainly the physical location of the catheter tip but not the extent of cell injury caused by the ablations. Therefore, as of today, RF ablation lesions are created with no information regarding the physiological condition of the affected tissue. This is problematic considering that gaps of excitable tissue between ablation lesions are directly related to arrhythmia recurrences. Monitoring tissue injury produced by ablation in real time remains a major limitation of current ablation approaches.

To resolve the problem of incomplete lesions, two main strategies have been proposed. The first is to improve ablation devices, which includes the development of multi-polar and linear catheters, balloon-based technologies using lasers and high-intensity focused ultrasound, as well as pressure-sensor equipped RF catheters.

The second strategy is to visualize RF ablation lesions during the ablation procedure. Such visualization can be based upon acute changes in the chemical and/or physical properties of the damaged tissue. Specifically, the current visualization proposals require the use of a dye and include magnetic resonance imaging (MRI), coherence tomography (CT) and spectroscopy.

All these strategies use surrogates to predict the areas of the gaps and none has a real time direct visualization technique as we have designed. Despite all the current technology, pulmonary vein reconnections occur in 94% of patients after the first procedure. Atrial fibrillation recurrences after ablation procedures are 80-90% of the time due to pulmonary vein reconnection at the sites of gaps.

SUMMARY

Systems and methods for visualizing ablated tissue are disclosed herein.

According to some aspects illustrated herein, there is provided a system for imaging tissue that includes a catheter having a distal end and a proximal end; an inflatable balloon disposed about the distal end of the catheter; and an optical housing extending from the distal end of the catheter into the balloon, the optical housing being configured to position inside the balloon a light source for illuminating a tissue outside the balloon and a camera for imaging the illuminated tissue.

According to some aspects illustrated herein, there is provided a system for imaging tissue that includes a catheter having a distal end and a proximal end; an inflatable balloon disposed about the distal end of the catheter; and an optical housing extending from the distal end of the catheter into the balloon; a light source inside the balloon, the light source being supported by the optical housing and configured to excite native reduced form of nicotinamide adenine dinucleotide or nicotinamide adenine dinucleotide hydrogen (NADH) in a tissue; and a camera inside the balloon, the camera being supported by the optical housing and configured to image the tissue illuminated by the light source.

According to some aspects illustrated herein, there is provided a system for imaging tissue that includes a catheter having a distal end and a proximal end; an irrigation port to displace blood with a fluid about the distal end of the catheter; and an optical housing extending from the distal end of the catheter, the optical housing being configured to support a light emitting diode light source for illuminating tissue and a visualization device including a plurality of image sensors that convert an optical image into an electronic signal for imaging the illuminated tissue.

According to some aspects illustrated herein, there is provided a system for imaging tissue that includes a sheath for infusing a fluid capable of displacing blood and transmitting light; a catheter disposed within the sheath, the catheter having a distal end and a proximal end; an optical housing extending from the distal end of the catheter, the optical housing being configured to support a light emitting diode light source for illuminating tissue and a visualization device including a plurality of image sensors that converts an optical image into an electronic signal for imaging the illuminated tissue.

According to some aspects illustrated herein, there is provided a method for imaging tissue that includes advancing to a tissue a catheter comprising an inflatable balloon disposed about the distal end of the catheter and an optical housing extending from the distal end of the catheter into the balloon to position a light source and a camera inside the balloon; ablating the tissue; illuminating with the light source an area of tissue including tissue treated by ablation and surrounding tissue to excite NADH in the area of tissue; imaging with an imaging device the area of tissue to detect NADH fluorescence of the area of tissue; and producing a display of the imaged, illuminated tissue, the display illustrating ablated tissue as having less fluorescence than non-ablated tissue.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 4A illustrates a RF ablation probe in the position to deliver a lesion onto the epicardial surface;

FIG. 4B illustrates the visual appearance of a typical lesion after a standard RF ablation protocol performed in a blood-free rat heart;

FIG. 4C illustrates the appearance of two distinct RF ablation lesions in a blood-free heart, as revealed by fNADH imaging;

FIG. 4D illustrates the appearance of the same two RF ablation lesions after TTC staining with vital TTC dye (white tissue—necrotic, red—viable);

FIG. 4E illustrates transverse slicing through TTC-stained heart showing depth of two lesions placed on opposite epicardial surfaces using two different power settings;

FIG. 8A, FIG. 8B, FIG. 8C and FIG. 8D illustrate profiles of fNADH and electrical activity across the isthmus between two RF lesions;

FIG. 9A, FIG. 9B, FIG. 9C and FIG. 9D illustrate RH237 retention within the ablation areas;

FIG. 10A is a schematic representation of lesion formation by RF catheter. FIGS. 10B and 10C show RF ablations done in rat hearts, and FIG. 10D shows RF ablations done in a rabbit heart;

As shown in FIG. 11D the ablated lesion is identified by lack of fluorescence which gives the tissue a dark appearance (center portion of the figure) whereas the ischemic or injured tissue becomes brighter as illustrated by the halo type appearance;

Figure 1A:
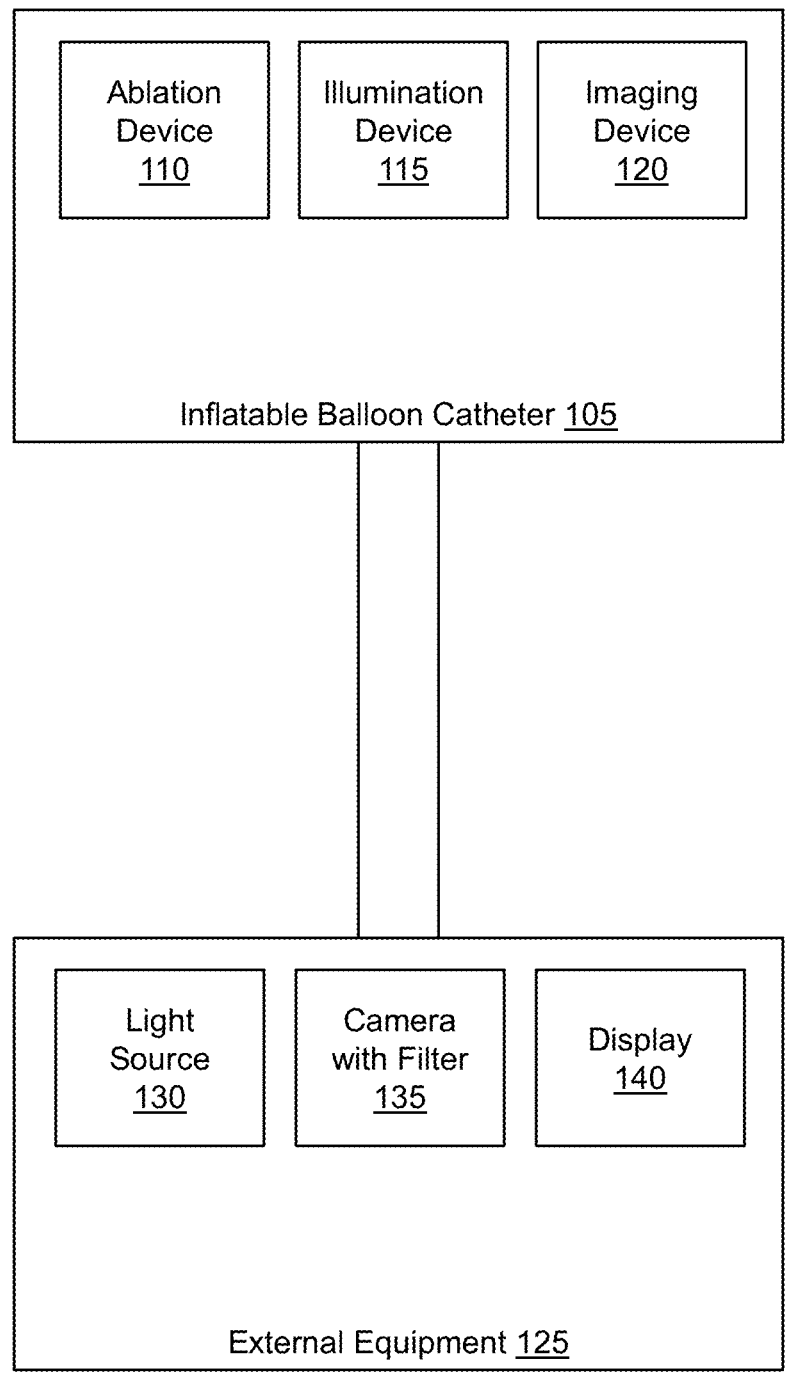
FIG. 1A is a block diagram of an exemplary system in accordance with the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Exemplary embodiments of the present disclosure are directed to systems and methods of visualizing RF ablation lesions during an ablation procedure. Systems and methods for treating Atrial Fibrillation (AF) are also provided.

Systems, catheter and methods for treating Atrial Fibrillation (AF) are provided. The fluorescence of endogenous NADH (fNADH) in heart tissue is imaged to identify ablated and unablated areas using a balloon guided catheter equipped with UV illumination source and UV capable fiber, a fluorescence capable camera or imaging bundle and optical band pass filter to detect NADH fluorescence. Gaps between ablated areas can be identified using the fNADH imaging and the gaps can then be ablated. The imaging can be performed during the ablation procedure and does not require additional chemicals, such as contrast agents, tracers or dyes.

In some embodiments, the systems of the present disclosure can be utilized to illuminate tissue using ultra-violet light and the fluorescence of endogenous NADH (fNADH) can be imaged to identify ablated and unablated areas. The provision of ultra-violet light and imaging of the fNADH of the tissue can be achieved using, for example, a dual UV excitation/emission fiber-optic waveguide located at the tip of the catheter. The methods and systems of the present disclosure do not require the addition of dyes and stains. Moreover, the methods and systems of the present disclosure allow imaging during the ablation procedure so as to not require an additional invasive ablation procedure following the initial procedure. Utilizing the methods and systems of the present disclosure results in having a completely dark area at the sites of complete ablation due to lack of fluorescence which may enhance the ability to detect the ablated areas by providing marked contrast to the healthy tissue and even more contrast at the border zone between ablated and healthy tissue. This border area is the edematous and ischemic tissue in which NADH fluorescence becomes bright white upon imaging. The border zone creates a halo appearance around the ablated central tissue.

In accordance with exemplary embodiments of the present disclosure, ablated tissue and tissue surrounding the ablated tissue is imaged using the fluorescence of endogenous NADH (fNADH) using low-intensity ultraviolet light illumination. NADH is a coenzyme that is present within intact cells and is particularly abundant in cardiac muscle cells. Once NADH is released from mitochondria of damaged cells and/or converted to its oxidized NAD+ form, cardiomyocyte fNADH markedly declines. This reveals the ablation-induced muscle injury to highlight gaps that indicate incomplete epicardial lesions.

Ablations are currently performed without meaningful real-time information regarding the physiology of the ablated tissue. Electrical isolation of focal sources is the only indicator of ablation efficiency. There are two main limitations of this approach. The first is that the extent of the lesions cannot be measured during the procedure. The second is that the specific cause of electrical isolation cannot be determined. For example, electrical isolation may result from cardiac muscle damage, but also from functional changes in reversibly injured cells, as well as by temporary edema. In the case of edema, it may subside after a few weeks, potentially restoring abnormal electrical conduction. The fNADH imaging of the present disclosure reveals irreversible cardiac muscle injury without contrast agents, tracers or dyes. Lesions examined via fNADH imaging are seen immediately after delivering RF energy and they are stable for several hours. Therefore, visualization can be done concordantly with ablation or after multiple lesions have been placed.

There is no contradiction between the increase in NADH fluorescence during ischemic injury used in the present disclosure as opposed to a decrease upon thermal damage due to the following reasons. About thirty percent of cardiomyocyte volume is comprised of mitochondria, which contain a large amount of NADH. Accordingly, changes in the level of fNADH from myocytes can be measured with relative ease. When the sarcolemma and mitochondrial membranes are disrupted by heat, NADH is lost and fNADH levels immediately fall. During hypoxia and/or ischemia, cellular integrity is preserved but oxygen availability is reduced. Oxygen serves as a final electron acceptor in the mitochondrial electron chain and its decline leads to NADH accumulation. Thus, ischemia causes an increase in fNADH in a time dependent manner. For example, if coronary perfusion is temporarily disrupted during ablation, patches of ischemic or injured tissue with elevated fNADH levels may be observed adjacent to the darker circular fNADH lesions after ablation, which can be seen in FIG. 4C.

Monitoring endogenous fNADH can be done without additional tracers or contrast agents. Since changes in fluorescence reflect acute biochemical changes, lesions are seen almost immediately. Although imaging modalities such as MRI, C-arm CT, and contrast echocardiography are excellent tools in detecting parameters resulting from heat induced biophysical changes, contrast agents are required to visualize changes in real time. Additionally, while MRI and C-arm CT provide high spatial resolution, it could take up to 30 minutes to visualize cell necrosis. Echocardiography is faster but suffers from low spatial resolution and limited field of view. Other modalities based on physical tissue changes including alteration in tissue elasticity, impedance, or absorption have also been explored. While such strategies provide real-time feedback and may predict lesion size and depth, they also require significant data processing and don't provide direct visualization of the ablated region. It should, however, be noted that these well-known imaging methods may be used in combination with the methods of the present disclosure.

Today a majority of ablation procedures are endocardial but approximately 10 to 20% could be applied to the epicardium. Epicardial substrates are frequently observed for VT, including >20% of postinfarct VTs, and >30% of VTs from nonischemic cardiomyopathy, particularly for Chagas disease. Ablation of these epicardial substrates may use a percutaneous approach that involves the subxiphoid placement of sheaths into an intact, closed pericardial space. fNADH imaging is particularly useful for these procedures. Conventional endoscopes equipped with UV-compatible optics and light sensitive image capture devices would be suitable for this purpose. Air insufflation through the endoscope could be used to expand the pericardial space for adequate visualization of ablation sites. In a clinical setting, insufflation with carbon dioxide rather than air would likely reduce the risk of air embolization. fNADH imaging might also be used for endocardial procedures if blood is displaced using inflatable balloons in front of an endoscope.

The systems and methods of the present disclosure enable the user to monitor myocardial damage while performing an ablation. By doing so, clinical cardiac electrophysiologists may be able to shorten the time and improve the efficiency of ablation, minimize unnecessary tissue injury that may cause post ablation complications, and decrease post-ablation recurrence of arrhythmias and the need for follow-up ablations. fNADH imaging may also be useful for mechanistic studies of tissue injury near the ablation sites and for assessment of drugs that may alter electrical propagation between inter-lesion gaps.

The use of fNADH imaging allows visualizing of ablation lesions and gaps between lesions in both blood-free and blood-perfused rat and rabbit hearts. Optical action potentials and the endogenous fluorescence of NADH can be imaged to study changes in electrical activity and tissue viability around ablation lesions. The fNADH imaging can be accomplished during ablation procedures using a dual UV excitation/emission fiber-optic waveguide located at the tip of a catheter. Such a waveguide system could interface with a 3D mapping system to provide a detailed map of cardiac muscle viability near the catheter.

FIG. 1A is a block diagram of an exemplary system in accordance with the present disclosure. The system includes an inflatable balloon catheter 105 coupled to external equipment 125. In some embodiments, the catheter 105 includes an ablation device 110, illumination device 115 and an imaging device 120. In some embodiments, the illumination device 115 and an imaging device 120 may utilize a fiber-optic waveguide to pass the light to and from the treated tissue.

In some embodiments, the methods and systems of the present disclosure may be used in connection with ablation procedures to monitor in real time when the complete ablation of desired tissue has been achieved. Ablation is a process that uses energy, heat or extreme cold (cryo) to destroy or damage tissue (ablation). For example, RF ablation relies on heat generated from the high frequency alternating current to ablate tissue. Cryoablation is used in a variety of clinical applications using hollow tubes or needles (cryoprobes) through which cooled, thermally conductive, fluids are circulated, to destroy the tissue by freezing the tissue. The systems and methods of the present disclosure may be utilized in connection with various types of tissue ablation, including, but not limited to, RF ablation, cryoablation, acoustic energy ablation, electromagnetic energy ablation, microwave energy ablation, ultrasound ablation, chemical ablation, laser ablation, thermal ablation, electrical ablation or other types of thermal or non-thermal energy ablations. To that end, in some embodiments, the ablation device 110 may be advanced to a tissue in need of ablation to ablate the tissue. In some embodiments, the ablation device 110 has an energy source selected from the group consisting of radiofrequency energy, microwave energy, electrical energy, electromagnetic energy, cryoenergy, laser energy, ultrasound energy, acoustic energy, chemical energy, and thermal energy.

The external equipment 125 includes a light source 130, which provides ultra-violet light to illumination device 115, a camera 135 and a display 140. In some embodiments, the camera 135 can be a CCD camera that has a high quantum efficiency for wavelengths corresponding to NADH fluorescence (i.e., 80% quantum efficiency at 460 nm), such as an Andor Ixon DV860 camera. In some embodiments, the camera 135 may be equipped with a 460/25 nm filter 135 (i.e., a filter to pass ultra-violet light while blocking light outside of the ultra-violet spectrum).

Figure 1B:
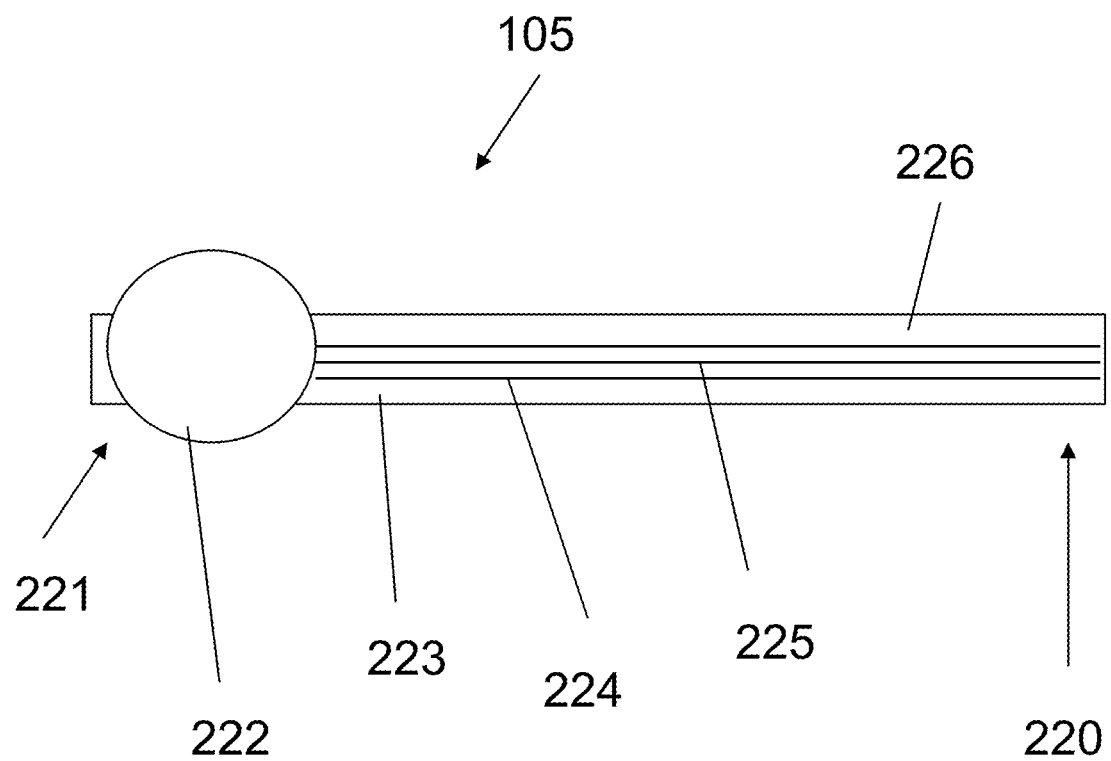
FIG. 1B illustrates an embodiment of a catheter for use in an exemplary system in accordance with the present disclosure.

In reference to FIG. 1B, in some embodiments, the catheter 105 is a multi-lumen catheter having a proximal end 220 and a distal end 221. The catheter 105 includes a balloon 222 disposed about the distal end 221 of the catheter 105. The balloon 222 may be made of a UV transparent material, such as, for example, a UV transparent fluoropolymer. In some embodiments, the balloon 222 may have a thickness of 50 μm and refractive index of 1.31. The balloon 222 may be either a complaint balloon or a non-complaint balloon.

The balloon 222 may be round, flat, cylindrical, oval, rectangular or another shape depending on the anatomy to be treated using the catheter 105. The balloon 222 may displace blood at the site of fluorescence imaging in order to afford an optically uncluttered view. Since blood possesses fluorescent properties mostly due to the hemoglobin, imaging through this medium would saturate the emission pathway. The balloon may be inflated with a gas or a liquid. For example, carbon dioxide, which has a low refractive index of about 1.00045, may be used to inflate the balloon. Also, in the event of a balloon breach in vivo, $CO_2$ exposure in the short term would not pose any immediate mortal danger due to the abundant partial pressure of $N_2$ gas. Suitable liquids include, but are not limited to, water, saline, blood or another similar liquid. The catheter 105 may include an inflation/deflation lumen 225 for inflating and deflating the balloon 222. Two separate lumens may be provided in some embodiments for inflating and deflating the balloon 222.

In addition to the inflation/deflation lumen 225, the catheter 105 may further include an ablation lumen 223 for advancing an ablation device 110, an imaging lumen 224 for advancing an imaging device 120, and an illumination lumen 226 for advancing an illumination device 115. It should of course be understood that the catheter 105 may include additional lumens or some lumens may serve multiple functions. For example, in some embodiments, a single fiber optic bundle may be employed to pass the light from a light source 130 to the tissue to illuminate the tissue and to pass the light reflected by the tissue to a camera 135.

Figure 1C:
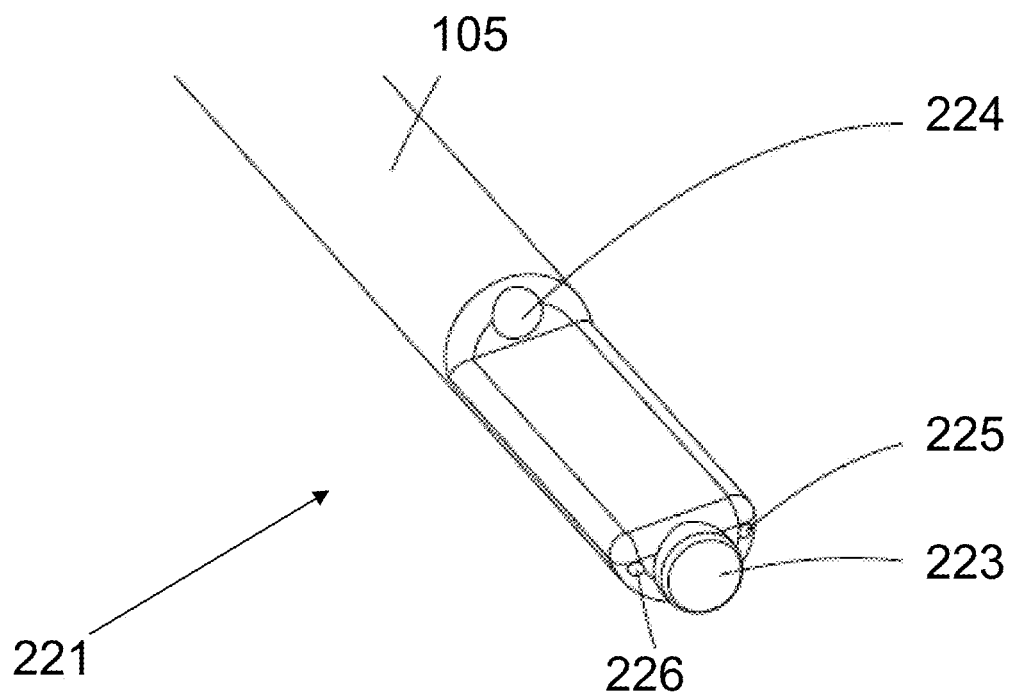
FIG. 1C illustrates a distal end of an embodiment of a catheter for use in an exemplary system in accordance with the present disclosure.

In reference to FIG. 1C, an embodiment of the distal tip 221 of the catheter 105 without the balloon 222 is illustrated. The ablation lumen 223 allows an ablation device 110 to be passed to or past the distal end 221 of the catheter 105 for ablation of desired tissue. The inflation/deflation lumen 225 enables the user to inflate and deflate the balloon 222 to aid in fluorescence imaging. The imaging lumen 224 allows an imaging device 120 to be advanced into the balloon for imaging the ablated tissue, which can be illuminated by an illumination device 105 advanced through the illumination lumen 226. It should of course be understood that, to the extent desired, the position of various lumens 223-226 in relation to one another may be varied.

Figure 1D:
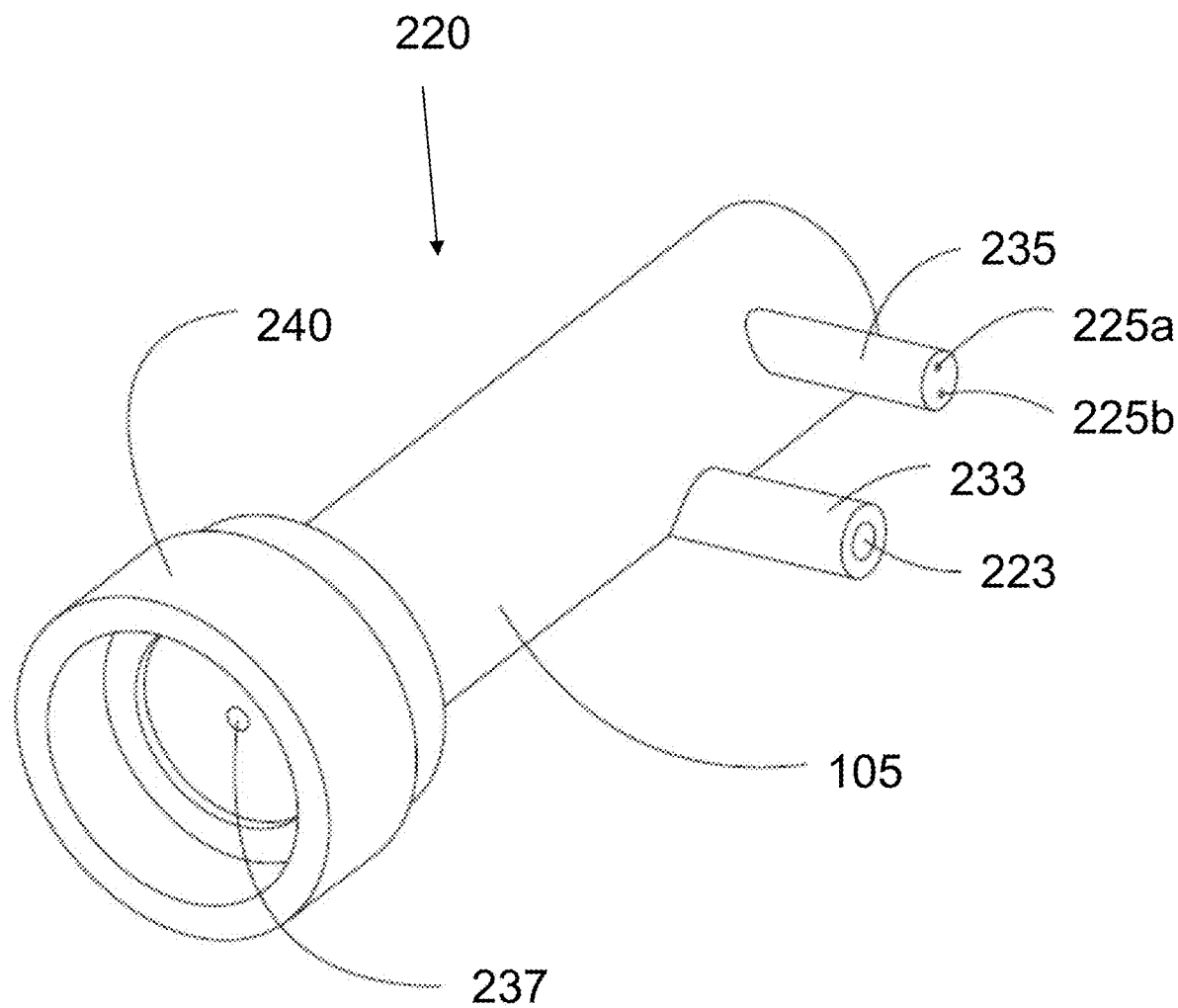
FIG. 1D illustrates a proximal end of an embodiment of a catheter for use in an exemplary system in accordance with the present disclosure.

In reference to FIG. 1D, an embodiment of the proximal tip 220 is illustrated. In some embodiments, an ablation port 233 in communication with the ablation lumen 223 may be provided for introducing an ablation device 110 into the catheter 105. Another port 235 may be provided in communication with the inflation lumen 225a and deflation lumen 225b for operating the balloon 222. In some embodiments, the proximal end 220 includes an outlet 237 in communication with the imaging lumen 224 and illumination lumen 226 to introduce an imaging device 120 and an illumination device 115 into the catheter 105. The catheter 105 may also be provided with a connector 240 for connecting the catheter 105 to one or more external equipment 125.

Referring back to FIG. 1A, the external equipment 125 may include a camera 135. In some embodiments, the camera 135 may be a CCD (charge-coupled device) camera. In some embodiments, the camera 135 may be selected so it is capable of collecting as many photons as possible and that contributes minimal noise to the image. Usually for fluorescence imaging of live cells, CCD cameras should have a quantum efficiency at about 460 nm of at least between 50-70%, indicating that 30-50% of photons will be disregarded. In some embodiments, the camera 135 has quantum efficiency at 460 of about 90%. The camera 135 may have a sample rate of 80 KHz. In some embodiments, the camera 135 may have a readout noise of 8 $e^-$ (electrons) or less. In some embodiments, the camera 135 has a minimum readout noise of $3e^-$.

The external equipment 125 may further include a light source 130, such as a UV LED emitter. The light source is utilized to illuminate tissue via an imaging device 120, which may comprise a fiber optic light guide and may be advanced through the imaging lumen 224 to the distal tip 221 of the catheter 105 to capture tissue images. In some embodiments, the fiber optic light guide can act as an illumination device 115 to pass the light at excitation wavelength from a light source 130 to the tissue for illuminating tissue to be visualized. The fiber optic light guide can also act to pass the light reflected by the tissue back to the camera 135. In some embodiments, separate fiber optics networks can be used for illumination and imaging that is, in some embodiments an illumination device 115 may be independent of the imaging device 120. In some embodiments, a fiberscope can be used as an imaging device, illumination device, or both.

Once the images of illuminated tissue are captured by the CCD, these images can be transmitted to a display 140 to be displayed to the user in real time. The images can be analyzed by using software to obtain real-time details (e.g. intensity or radiated energy in a specific site of the image) to help the user to determine whether further intervention is necessary or desirable.

Figure 2A:
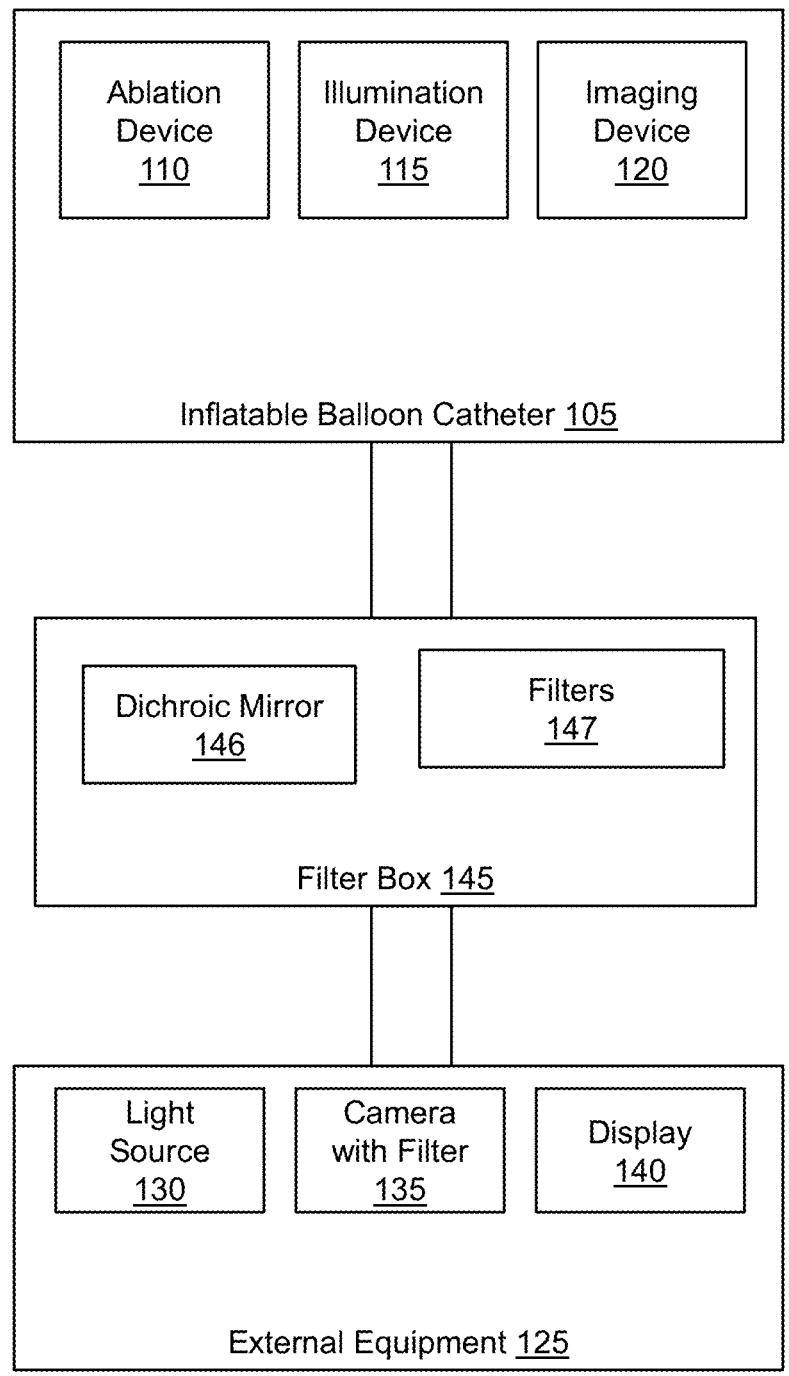
FIG. 2A is a block diagram of an exemplary system in accordance with the present disclosure.

In reference to FIG. 2A, in some embodiments, the system of the present disclosure may include a filter box 145 positioned between the catheter system 105 and the external equipment 125, such as the camera 135 and light source 130. The filter box 145 may include a dichroic mirror 146 for reflecting light from the light source 130 to be propagated by the illumination device 115. The dichroic mirror 146 may be placed at a 45° incidence angle to light, creating a stop band of reflected light and a pass band of transmitted light. Light from the light source 130 is reflected by 90° in the direction of the specimen. Concurrently, in the same orientation, light emanating from the specimen is passed through the mirror. In some embodiments, a longpass dichroic mirror with a cutoff (50%) wavelength of 425 nm may be used as it has an approximate reflection band of more than 80% between 355 nm and 410 nm and a transmission band of more than 90% between 440 nm and 700 nm. Of course it should be understood that other optical devices may be used to pass light to and from the tissue to be visualized.

The filter box 145 may also include an emission filter 147 to filter out light that may contribute as some sort of noise or unwanted feature. In some embodiments, based on the NADH fluorescence, the filter 147 may be a center wavelength of 460 nm with a 50-nm bandwidth (i.e. 460 nm±25 nm). The filter box 145 may further include an excitation filter for selection of the excitation wavelength of light from the light source 130.

Figure 2B:
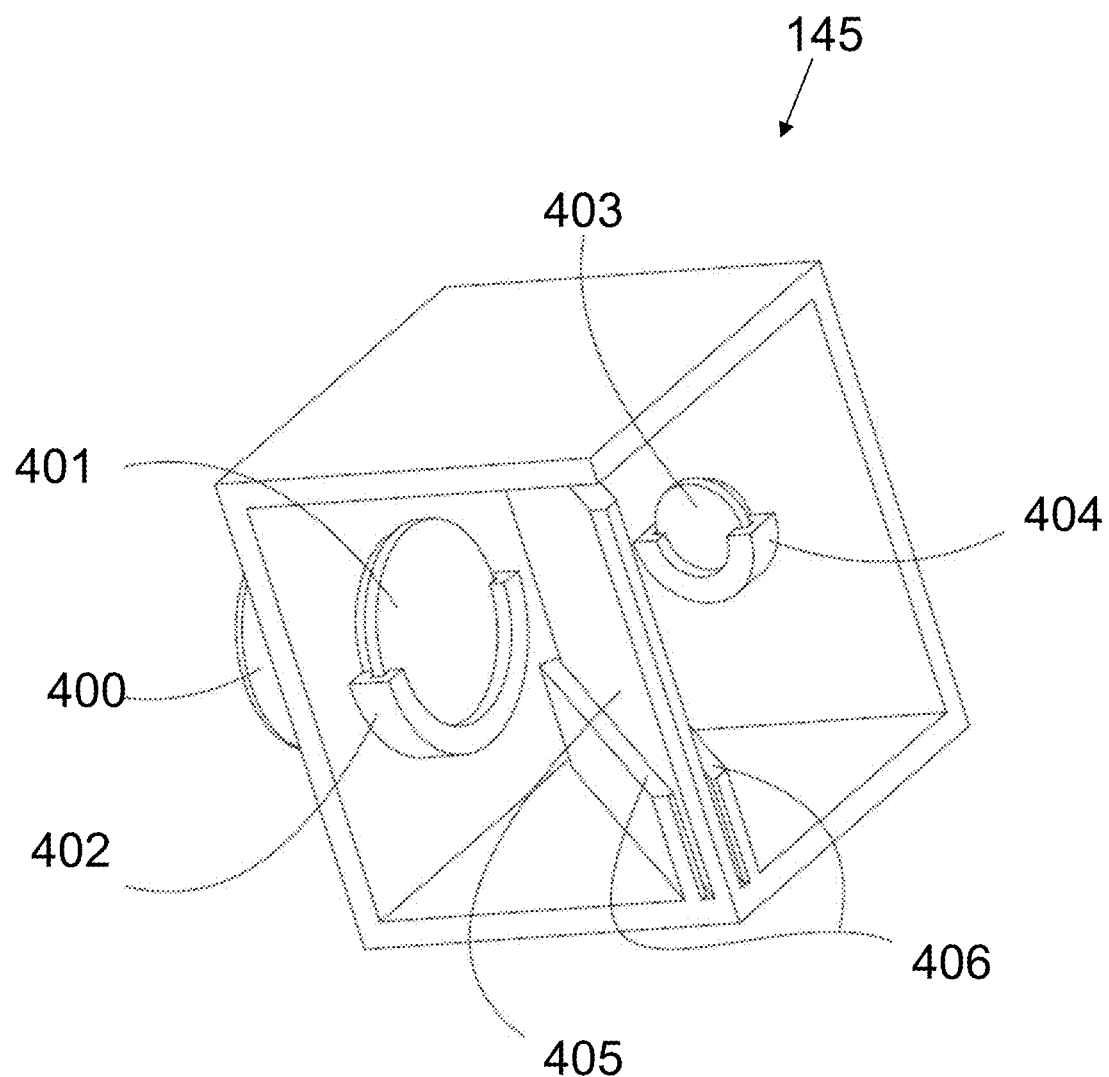
FIG. 2B illustrates an embodiment filter box for use in connection with the exemplary system shown in FIG. 2A.

In reference to FIG. 2B, an embodiment filter box 145 includes a camera port 400 with an emission filter 401 held in a filter holder 402 positioned in front of the camera port 400. The filter box 145 further includes an excitation filter 403 held in a filter holder 404, which may be positioned either at a light source port or a catheter port. The excitation filter 403 is positioned at a catheter port 405. A dichroic mirror 405 is inserted into a mirror slot 406 and is positioned at about a 45 degree angle to a port for attaching the light source 130 to the filter box 145.

Figure 3:
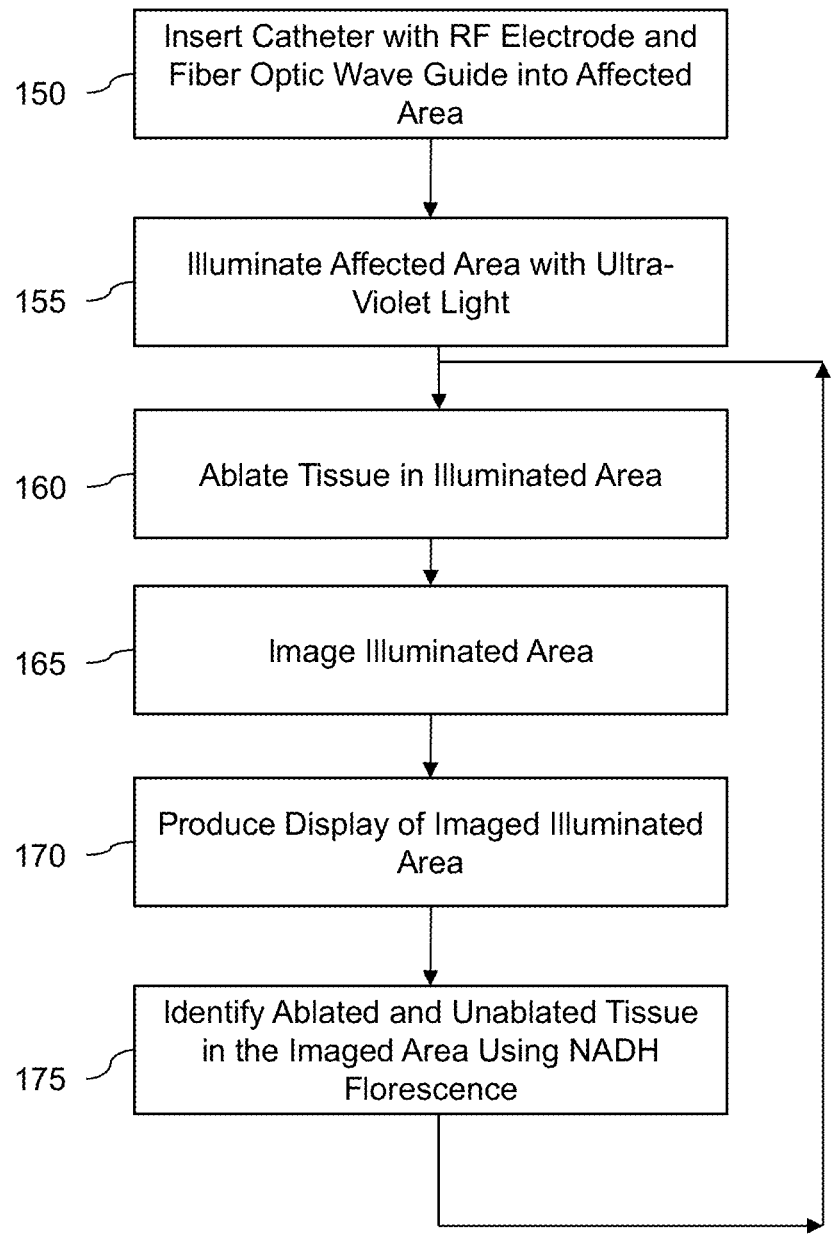
FIG. 3 is a flow diagram of an exemplary method in accordance with the present disclosure.

In reference to FIG. 3, operation of the systems of the present disclosure is illustrated. Initially, catheter 105 is inserted into the area affected by the atrial fibrillation, such as the pulmonary vein/left atrial junction (step 150). Blood is removed from the visual field. For atrial fibrillation ablation a transparent balloon surrounding the fiber optic waveguide would be used to displace the blood at the pulmonary vein/left atrial junction. The affected area is illuminated by ultra-violet light from source 130 and illumination device 115 (step 155) and tissue in the illuminated area is ablated using ablation device 110 (step 160). Either point-to-point RF ablation or cryoablation or laser or other known ablation procedures may be employed using the systems of the present disclosure. Ablation proceeds by threading the tip through the central lumen of the catheter. After the procedure, the ablation tip may be retracted.

The illuminated area is imaged by the combination of imaging device 120 and camera 135 (step 165). The methods of the present disclosure rely on imaging of the fluorescence emission of NADH, which is a reduced form of nicotinamide adenine dinucleotide (NAD+). NAD+ is a coenzyme that plays important roles in the aerobic metabolic redox reactions of all living cells. It acts as an oxidizing agent by accepting electrons from citric acid cycle (tricarboxylic acid cycle), which occurs in the mitochondrion. By this process, NAD+ is thus reduced to NADH. NADH and NAD+ are most abundant in the respiratory unit of the cell, the mitochondria, but are also present in the cytoplasm. NADH is an electron and proton donor in mitochondria to regulate the metabolism of the cell and to participate in many biological processes including DNA repair and transcription.

By measuring the UV-induced fluorescence of tissue, it is possible to learn about the biochemical state of the tissue. NADH fluorescence has been studied for its use in monitoring cell metabolic activities and cell death. Several studies in vitro and in vivo investigated the potential of using NADH fluorescence intensity as an intrinsic biomarker of cell death (either apoptosis or necrosis) monitoring. Once NADH is released from the mitochondria of damaged cells or converted to its oxidized form (NAD+), its fluorescence markedly declines, thus making it very useful in the differentiation of a healthy tissue from a damaged tissue. NADH can accumulate in the cell during ischemic states when oxygen is not available, increasing the fluorescent intensity. However, NADH presence disappears all together in the case of a dead cell. The following table summarizes the different states of relative intensity due to NADH fluorescence:

| Cellular State | NADH Presence | Relative Changes of Autofluorescense intensity |
| --- | --- | --- |
| Metabolically Active | Normal | Baseline |
| Metabolically Active but Impaired (Ischemia) | Increased to Hypoxia | Increased |
| Metabolically Inactive (Necrotic) | None | Full Attenuation |

While both NAD+ and NADH absorb UV light quite readily, NADH is autofluorescent in response to UV excitation whereas NAD+ is not. NADH has a UV excitation peak of about 350-360 nm and an emission peak of about 460 nm. In some embodiments, the methods of the present disclosure may employ excitation wavelengths between about 335 to about 380 nm. With the proper instrumentation, it is thus possible to image the emission wavelengths as a real-time measure of hypoxia as well as necrotic tissue within a region of interest. Furthermore, a relative metric can be realized with a grayscale rendering proportionate to NADH fluorescence.

Under hypoxic conditions, the oxygen levels decline. The subsequent fNADH emission signal may increase in intensity indicating an excess of mitochondrial NADH. If hypoxia is left unchecked, full attenuation of the signal will ultimately occur as the affected cells along with their mitochondria die. High contrast in NADH levels may be used to identify the perimeter of terminally damaged ablated tissue.

To initiate fluorescence imaging, the operator may deploy the balloon, which is installed around the distal portion of the catheter. Next, NADH is excited by the UV light from the light source 130. In some embodiments with a filter box, first the excitation light from the light source hits the dichromatic mirror (or dichroic beam splitter) positioned within the filter box 145. Then the excitation light is reflected by the dichromatic mirror toward the specimen via the fiber optic. In some embodiments, the mirror may be positioned at a 45° angle relative to the excitation light and the excitation light may be reflected 90°. In some embodiments, the methods of the present disclosure may employ excitation wavelengths between about 335 to about 380 nm.

NADH in the tissue specimen absorbs the excitation wavelengths of light and emit longer wavelengths of light. The emission light may be collected and passed back through the dichromatic mirror 146. This mirror 146 may therefore be designed to reflect the excitation wavelengths, but transmit the emission wavelengths. The reflection of the excitation wavelengths is not 100%, so a small amount of this light passes through the dichromatic mirror 146. Likewise, additional light with a different wavelength could pass through, and thus an emission filter may be employed in connection with the camera 135. The emission filter may be selected for the emission wavelengths of light expected from the fluorophore such as NADH.

Once the light is filtered, the light may be collected by the camera 135, and a display of the imaged illuminated area is produced on display 140 (step 170), which is used to identify the ablated and unablated tissue in the imaged area using NADH florescence (step 175). The process then repeats by returning to the ablation step, if necessary to ablate additional tissue. It should be recognized that although FIG. 3 illustrates the steps being performed sequentially, many of the steps will be performed simultaneously or nearly simultaneously. Thus, for example, the ablation, imaging and display can occur at the same time, and the identification of the ablated and unablated tissue can occur while ablating the tissue.

The methods, systems and devices disclosed herein can be used for a variety of therapeutic procedures. Exemplary procedures in which the methods, systems and devices disclosed herein can be utilized include, but not limited to, for diagnostic and therapeutic procedures in the heart, for treating arrhythmias, such as, for example, supraventricular arrhythmias and ventricular arrhythmias, for treating atrial fibrillation, and pulmonary vein mapping and ablation. The ablated tissue may be cardiac muscle, but the methods disclosed herein should have the same effect on skeletal muscle, liver, kidney, and other tissues with significant presence of NADH-rich mitochondria.

Figure 16:
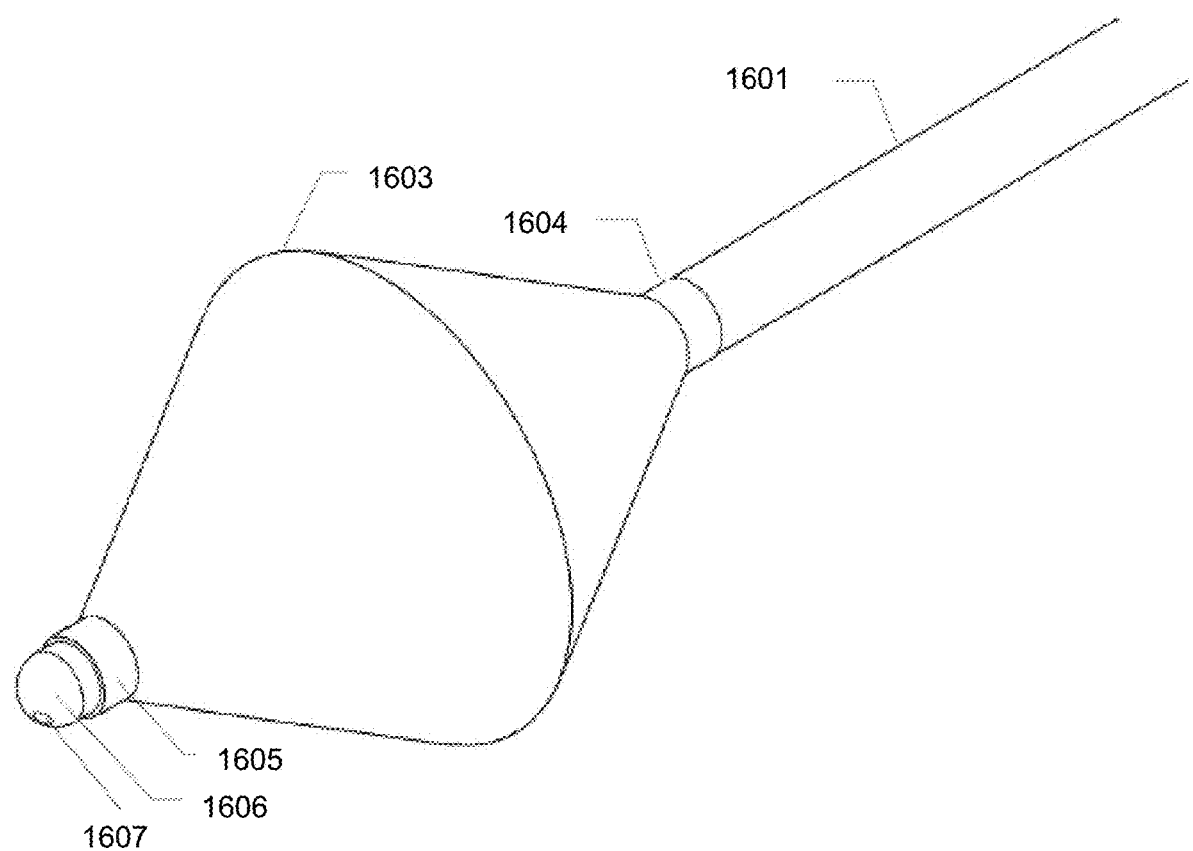
FIG. 16 is a view of an embodiment of the balloon catheter assembly of the present disclosure.

In reference to FIG. 16, a catheter 1601 for use in connection with systems and methods of the present disclosure includes one or more lumens extending therethrough and an expandable balloon 1603 disposed about the distal end of the catheter 1601. In some embodiments, the balloon 1603 may be attached at its proximal tip 1604 to the distal end of the body of the catheter 1601 and attached at its distal tip 1605 to a catheter tip 1606, which may be connected to the catheter 1601 by a tube or lumen as described below. The balloon 1603 may be made from an optically transparent material and may be used to move blood out of the way for the optical components during fluorescence imaging. The balloon 1603 can be made of many different materials and shapes that would best conform to various anatomic structures. The balloons may be constructed of a soft material, such as silicone, and be compliant to the anatomy. Alternatively, the balloon may be constructed of a stronger material, such as polyurethane, and be less compliant. As illustrated in FIG. 16, the balloon 1603 may have a conical shape designed for insertion into the ostium of the pulmonary veins. Other shapes of a more circular nature may be better suited for visualizing other cardiac anatomical sights for ablation therapy, including, by way of a non-limiting example, accessory pathways, ventricular wall sites, atrial wall sights, or atrio-ventricular nodal sights.

The catheter 1601 may be utilized for tissue ablation, including, but not limited to, RF ablation, cryoablation, acoustic energy ablation, electromagnetic energy ablation, microwave energy ablation, ultrasound ablation, chemical ablation, laser ablation, thermal ablation, electrical ablation or other types of thermal or non-thermal energy ablations. To that end, in some embodiments, the catheter 1601 may be advanced to a tissue in need of ablation and an ablation member capable of performing one more ablation methods can be passed through the catheter 1601 to ablate the tissue. In some embodiments, the ablation member has an energy source selected from the group consisting of radiofrequency energy, microwave energy, electrical energy, electromagnetic energy, cryoenergy, laser energy, ultrasound energy, acoustic energy, chemical energy, and thermal energy.

In some embodiments, the catheter tip 1606 may be configured to act as an electrode either for diagnostic purposes, such as electrogram sensing, or for therapeutic purposes, such as for emitting ablation energy. In some embodiments where ablation energy is required of the catheter, the tip 1606 of the catheter 1601 could serve as an ablation electrode or ablation element. In the embodiments where RF energy is implemented, the wiring to couple the tip to the RF energy source (external to the catheter) can be passed through a lumen of the catheter 1601. The tip 1606 may include a port 1607 in communication with the one or more lumens of the catheter 1601. In this manner, a guide wire or other surgical instruments, such as, for example, an RF electrode, may be advanced out of the catheter 1601 past the tip 1606. The tip 1606 can be made of any biocompatible material. In some embodiments, if the tip is configured to act as an electrode, the tip 1606 can be made of metal, including, but not limited to, platinum, platinized iridium, stainless steel, or titanium. The tip 1606 may also be made of a biocompatible plastic, including, but not limited to, silicone, peek, polyurethane.

Figure 17:
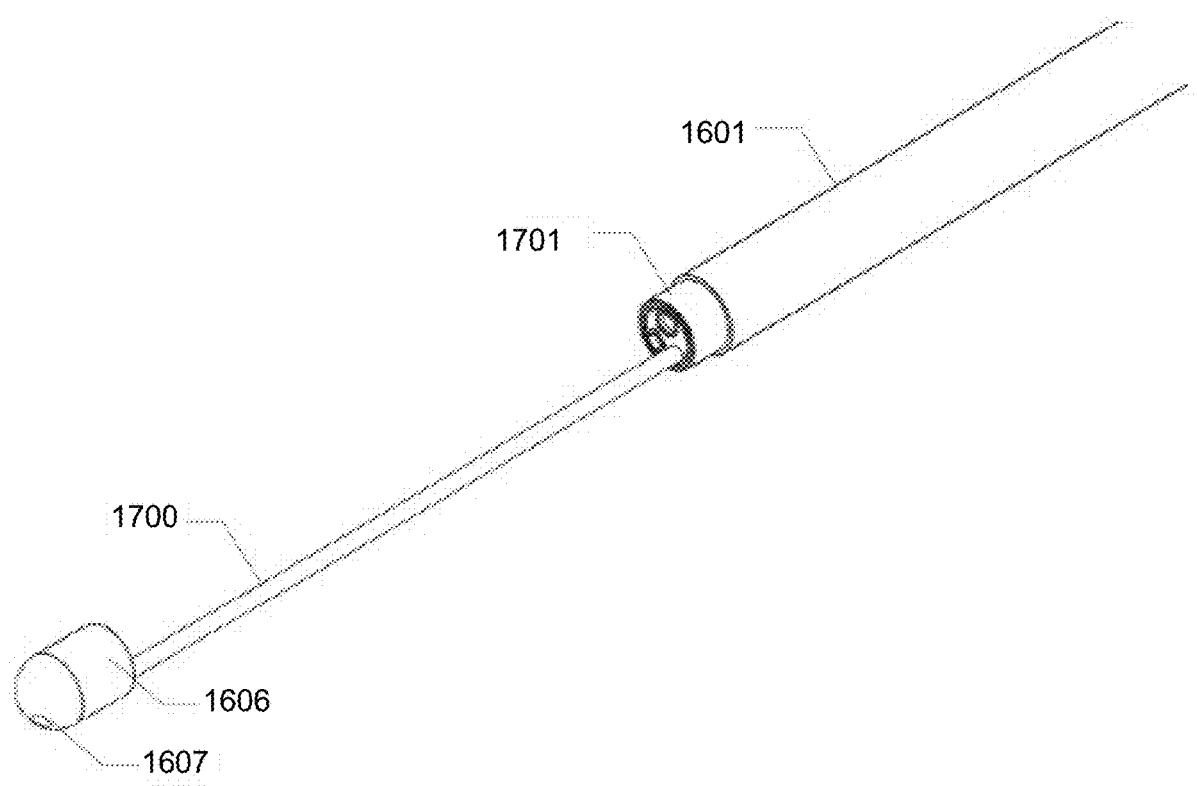
FIG. 17 is a view of an embodiment of the balloon catheter assembly of the present disclosure with balloon hidden.

In reference to FIG. 17, in some embodiments, the catheter tip 1606 may be connected to the main body of the catheter 1601 by a guide wire tube 1700 extend past distal tip of the main body of the catheter 1601. The guide wire tube 1700 may include one or more lumens in communication with one or more lumens of the catheter 1601 for advancing a guide wire, ablation member or other surgical instruments past the distal tip of the catheter 1601. The inner lumens of the guide wire tube 1700 may also be in communication with the port 1607 of the catheter tip 1606 for advancing surgical instruments through the guide wire tube 1700 to or past the catheter tip 1606.

In some embodiments, the guide wire tube 1700 may act to provide structural support to the balloon 1603, especially when the balloon 1603 is in a deflated state during the advancement of the catheter 1601 to the treatment site. In some embodiments, the guide wire tube 1700 may be semi-rigid to provide structural support to the balloon 1603. In some embodiments, the guide wire tube 1700 may be an integral lumen of the catheter 1601. In some embodiments, the guide wire tube 1700 is separate from the catheter 1601 and may be removable inserted into the distal tip of the catheter 1601. In some embodiments, the guide wire tube 1700 may be slidable disposed within the catheter 1601, so that the guide wire tube 1700 may be moved in relation to the catheter 1601 to adjust the shape of the balloon 1603 to aid in advancement or withdrawal of the catheter 1601 from the patient's body. For example, the guide wire tube 1700 may be advanced to stretch a collapsed balloon for easier withdrawal out of the patient's body. In such a state, the balloon would be more behaved and less likely to get caught on an introducer sheath when being removed. The guide wire tube may be made of any material. In some embodiments, the guide wire tube 1700 may be made from a shape memory material, such as Nitinol.

In reference to FIG. 17 in combination with FIG. 16, the catheter 1601 may include a neck down surface 1701 where the proximal end 1604 of the balloon 1603 may be attached to the catheter 1601 without increasing the outer diameter of the combined device.

Figure 18:
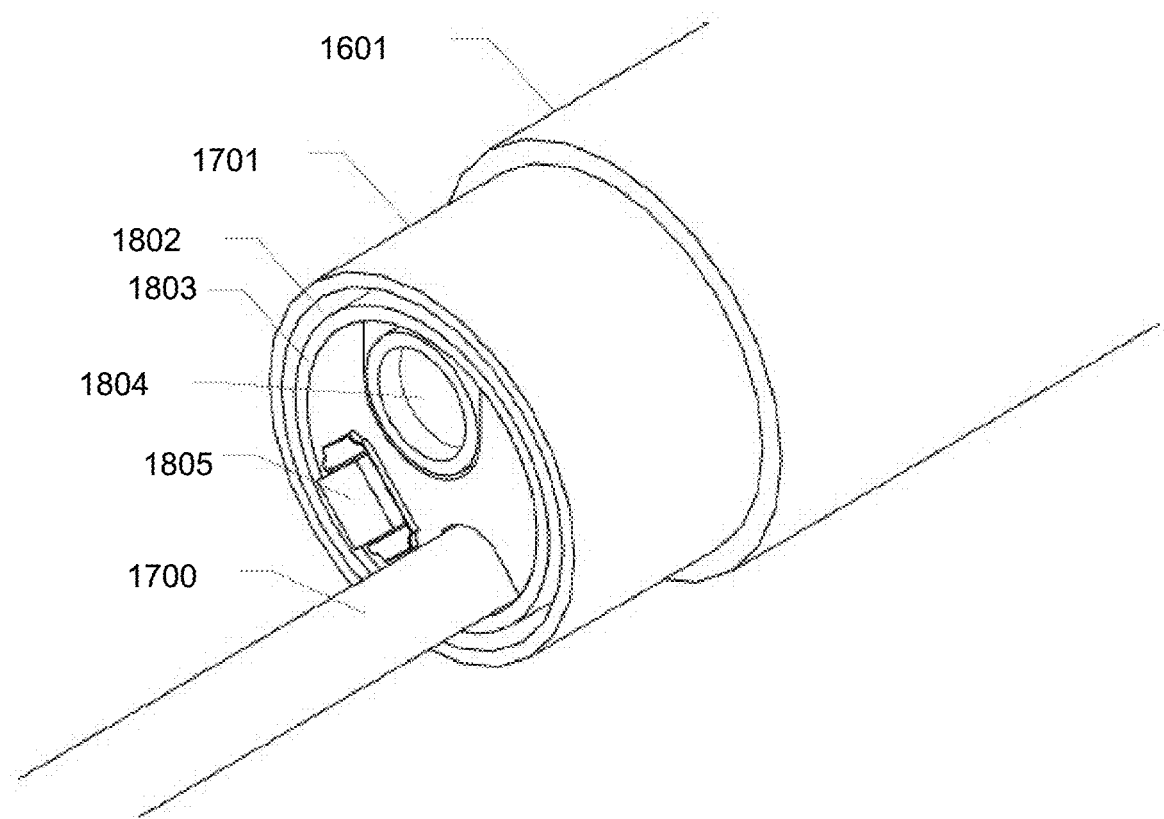
FIG. 18 is a view of an embodiment optical housing inserted into an embodiment catheter of the present disclosure.

In reference to FIG. 18, an optical housing 1803 may be disposed at the distal end of the catheter 1601 for positioning optical elements, such as a camera 1804 and a light source 1805, inside the balloon 1603. The optical housing 1803 enables positioning of the camera 1804 and light source 1805 within the balloon, thus eliminating the need for an external light source. Moreover, by putting the light sources within the balloon, wider angles of illumination may be achieved than when using a fiber bundle. As is shown in FIG. 18, the optical housing 1803 can extend from the catheter into the balloon such that the light source and the camera are completely contained within the balloon to ensure that the catheter does not interfere with the field of view of the light source or the camera. As shown in FIG. 18, that the light source and the camera are internal to the balloon and do not extend outside the balloon. In some embodiments, the housing 1803 may position the optical elements in a fixed relation to one another. In some embodiments, the camera 1804 and the light source 1805 are flush with each other so that neither component "blocks" the function of the other. Being flush assures that the camera 1804 will not block illumination nor will the light source 1805 show up in the camera image. In some embodiments, the position of the components may altered to avoid interference of one optical component with the other one.

The camera 1804 may be any image sensor that can convert an optical image into an electronic signal. In some embodiments, the camera is a miniature CMOS image sensor with a lens and with or without a filter to choose a specific wavelength or set of wavelengths to record. In some embodiments, the camera is a CCD camera or other image sensors that can convert an optical image into an electronic signal. The camera may transmit its signal via wires to external image processor and video terminal for the physician to see. In some embodiments, the camera may have wireless communication capabilities for communication with external devices. The light source 1805 may be a light emitting diode (LED) of suitable wavelength. In some embodiments, the LED will have a wavelength in the UV range to cause the NADH fluorescence. In some embodiments, different wavelengths including white light for multicolor illumination are possible by choosing the LED of the appropriate wavelength. By way of a non-limiting example, suitable LEDs for UV applications would include those with wavelengths of 300 nm to 400 nm, while suitable LEDs for visible or white light applications would include those with color temperature ranges from 2000K to 8000K.

As shown in FIG. 18, the housing 1803 may be inserted into the distal end of the catheter 1601. In some embodiments, the outer diameter of the housing 1803 may be smaller than the inner diameter of the catheter 1601 such that a gap 1802 may be formed between the inner wall of the catheter 1601 and the housing 1803. In some embodiments, the balloon 1603 may be deflated or inflated through the gap 1802. It should of course be understood that a separate lumen may be provided for operating the balloon 1603.

In some embodiments, because the outer diameter of the optical housing 1803 is smaller than the inner diameter of the catheter 1601, the housing 1803 may be moveable in relation to the catheter 1601. In some embodiments, the housing 1803 may be freely rotated in relation to the catheter 1601 and, thus the balloon 1603. In some embodiments, the optical housing 1803 may be translated longitudinally in relation to the balloon catheter 1601 to obtain a desired view point for the camera or illumination position for the light source. A lock may be provided to lock the optical housing 1803 in a desired position.

Figure 19:
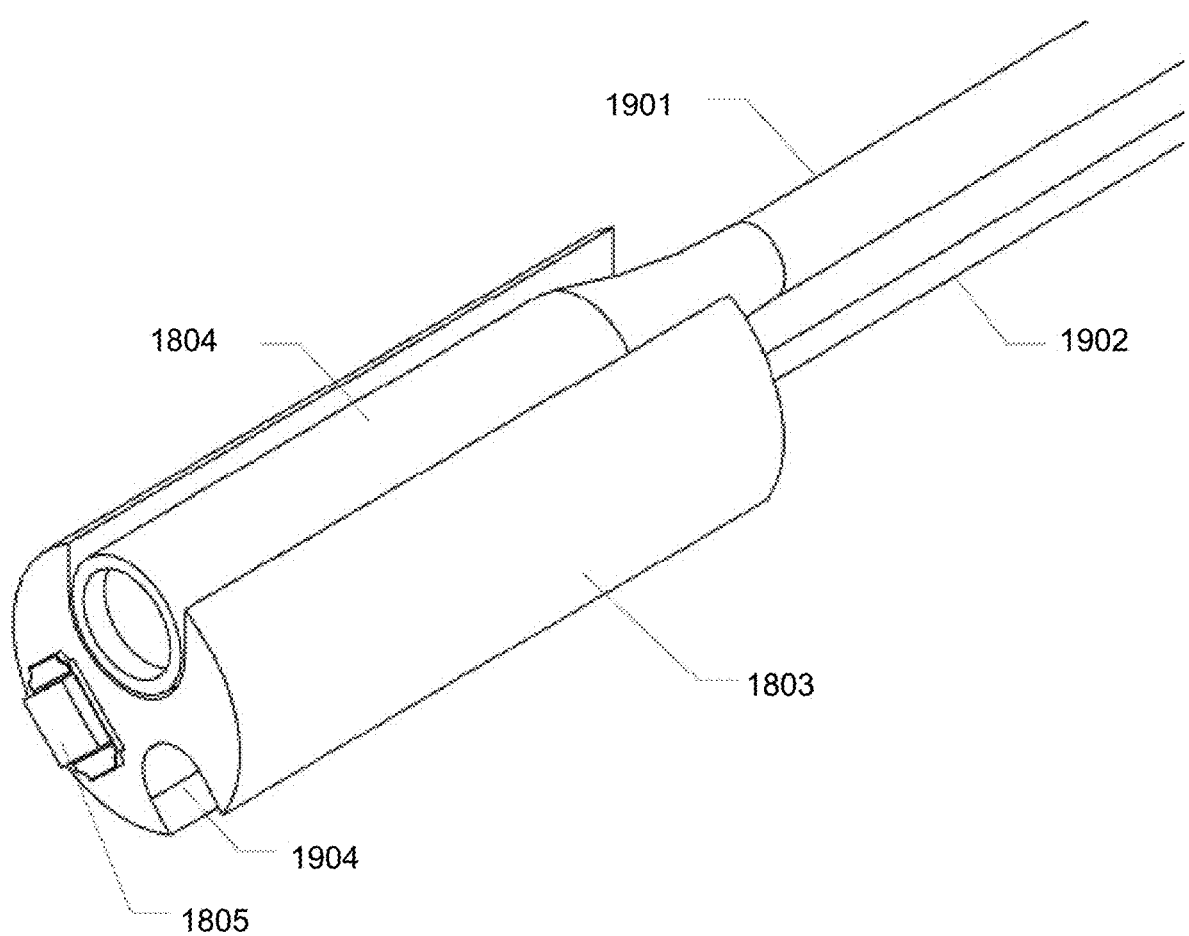
FIG. 19, FIG. 20 and FIG. 21 illustrate various non-limiting embodiments of an optical housing of the present disclosure.

FIG. 19 is a view of the housing 1803 outside the catheter 1601, showing a wire bundle 1901 of the camera 1804 and a wire bundle 1902 for the light source 1805. These wire bundles may run the entire length of the catheter back to the handle (not shown) where they can make electrical connections to the remainder of the imaging system, such as a power source or a display. It should be noted however that, in some embodiments, the camera may have wireless communication capabilities for wireless communication with external devices The housing 1803 also includes a channel 1904 for accepting a guide wire tube 1700 to facilitate communication between the guide wire tube 1700 and the catheter 1601.

The catheters of the present disclosure may be used in minimally-invasive procedures as well as in conventional surgical procedures, i.e. open procedures. In some embodiments, the catheters of the present disclosure may be configured for endovascular approach. In some embodiments, the catheters of the present disclosure may be configured for non-endovascular approach. In some embodiments, the systems of the present disclosure may be surgical systems or device used in surgical procedures via either an open incision or percutaneous introduction into the tissue rather than via an endovascular route. In some embodiments, the systems and devices of the present disclosure may be either handheld or a part of a robotically controlled system. In some embodiments, the systems or devices of the present disclosure may configured for handling by a robotic system.

In some embodiments, the size of the components may be varied depending on the particular procedure. In some embodiments, the rigidity of the catheters of the present disclosure may be varied depending on the type of procedure, anatomy to be treated or both. In some embodiments, the rigidity may be varied by selecting more rigid components for the catheter 1601, the guide wire tube 1700 or both.

Figure 20:
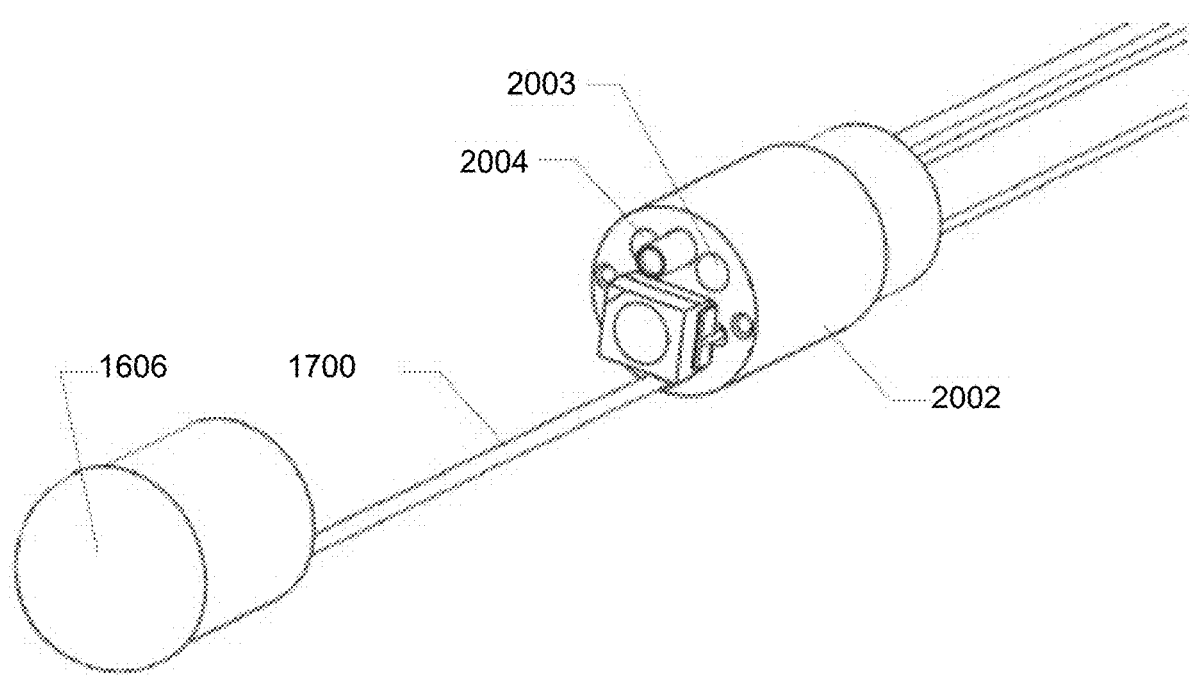

In reference to FIG. 20, in some embodiments, an optical housing 2002 may include multiple channels 2003, 2004 for accommodating multiple guide wire tubes, if more rigidity is required. It should be noted that in various embodiments, some or all guide wire tubes may include inner lumens in communication with the inner lumens of the catheter 1601 and the port 1607 of the catheter tip 1606 for passing surgical instruments through such guide wire tubes. In some embodiments, some or all guide wire tubes may act simply be provided for structural support, and thus may not include inner lumens.

Figure 21:
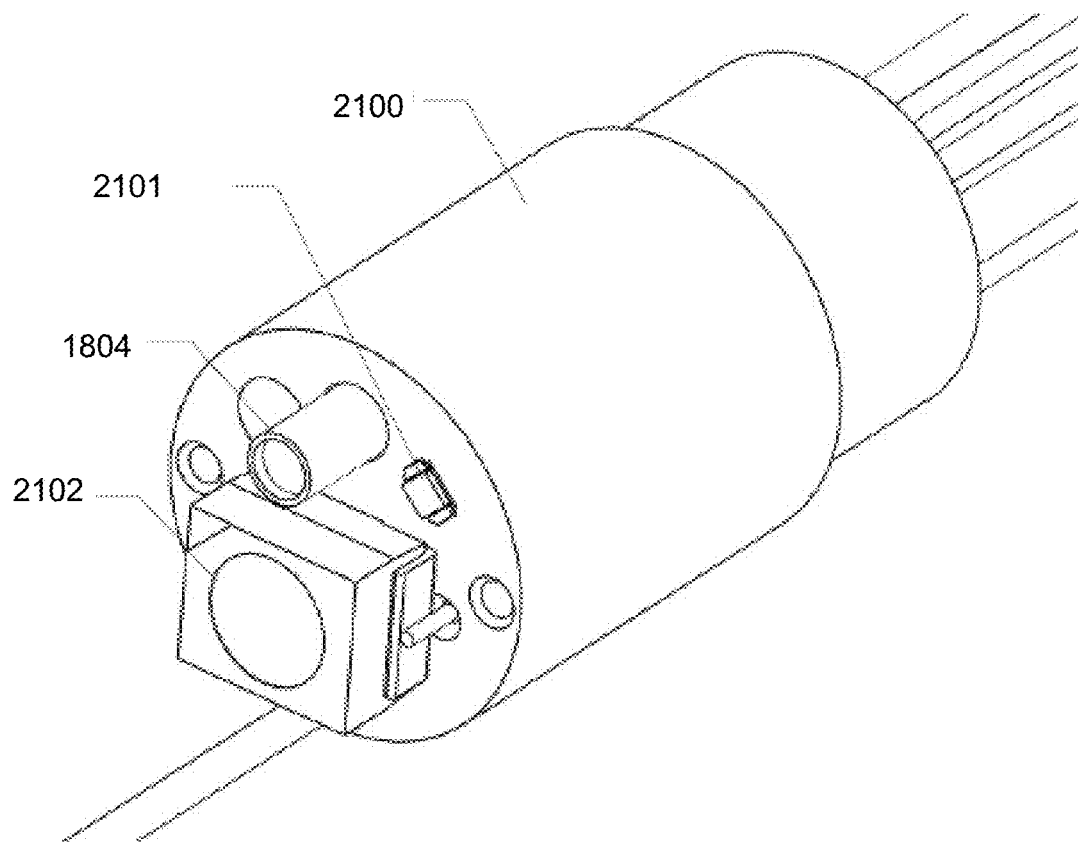

FIG. 21 illustrates an embodiment of an optical housing 2100 configured to support multiple light sources 2101 and 2102, which may emit light of different wavelengths. Having different wavelength sources allows for different functionality within a single catheter or instrument. In some embodiments, the light source 2101 may be selected to emit UV light for fluorescence imaging, while the light source 2102 may be selected to emit white light to allow the user to see and navigate anatomical landmarks. Bundled together, the user can use the same catheter both for navigating to the ablation site to ablate tissue, and then to visualize the ablated tissue. In some embodiments, multiple sources of the same wavelength may be employed. In some embodiments, the optical housing 2100 may be configured to support two, three, four or more light sources.

It should be noted that although the optical housing 1803 is illustrated and describe as supporting a light source and camera, in some embodiments, the housing may be configured to support one or more fiber optic bundles in communication with an external camera and an external light source.

The methods, systems and devices disclosed herein can be used for a variety of therapeutic procedures. Exemplary procedures in which the methods, systems and devices disclosed herein can be utilized include, but not limited to, for diagnostic and therapeutic procedures in the heart, for treating arrhythmias, such as, for example, supraventricular arrhythmias and ventricular arrhythmias, for treating atrial fibrillation, and pulmonary vein mapping and ablation.

The presently disclosed methods can be used with two dimensional (2D) to three dimensional (3D) mapping protocols. A plurality of 2D images can be superimposed onto a 3D reconstruction image of the tissue or organs, including the heart. Many arrhythmia procedures include the use of reconstructed three dimension images of the patient's specific anatomy during the procedure. Using a variety of imaging modalities including computed tomography (CT), magnetic resonance imaging (MRI), ultrasound, and electroanatomical mapping using systems such as NAVX and CARTO. In all cases, the three dimensional anatomical images or surfaces present patient specific anatomy to help target areas of tissue to treat. In all cases, the ability to visualize the precise location where lesions are formed and the precise locations where lesions are missing, e.g., the "gaps" or breaks in the lesion set, would guide the procedure to optimize the therapeutic outcome. 2D image to 3D image mapping allows the system to superimpose, spatially register, and/or texture map single or multiple images of tissue (that may indicate presence or absence of lesions) with the specific anatomy of the patient in a three dimensional, rotatable, interactive virtual environment.

In some embodiments, the systems and methods of the present disclosure allow the registration and/or overlay of the images produced by the system onto the specific anatomy of the patient as seen using other imaging modalities such as an MRI image, computed tomography (CT) image, ultrasound image and three dimensional reconstructions thereof. In some embodiments, the systems and methods of the present disclosure may further include the registration and/or overlay of the images produced by the system onto the specific anatomy of the patient as seen using other electroanatomical mapping, anatomical reconstruction, and navigational systems such as NAVX and CARTO. The registration and overlay may be performed during the procedure in real time. Texture mapping NADH images onto reconstructed endocardial surfaces permits visualization of the treatment site. For example, multiple NADH snapshots of lesions could create a full panoramic image of the entire pulmonary vein opening, or multiple pulmonary veins. Positioning sensors on the catheter tip could provide information that will allow the NADH images to be combined together to create a 3D reconstruction image.

While the methods and systems of the present disclosure were described in connection with a balloon catheter, the methods and systems of the present disclosure may also utilize catheters without balloons. Other means for displacing blood during fluorescence imaging may be utilized. For example, the catheter of the present disclosure may be provided with an irrigation port through which a fluid can be delivered to the distal tip of the catheter to displace blood away from the tissue being imaged. In some embodiments, the catheter may be introduced through a sheath which can infuse a clear fluid capable of displacing blood and transmitting light. It should of course be understood that, in some embodiments, the means for displacement blood may be combined. Thus, for example, a balloon catheter as described above can be provided with additional irrigation port to assist in blood displacement by the balloon.

Examples of using the systems and methods of the present disclosure are provided below. These examples are merely representative and should not be used to limit the scope of the present disclosure. A large variety of alternative designs exists for the methods and devices disclosed herein. The selected examples are therefore used mostly to demonstrate the principles of the devices and methods disclosed herein.

EXAMPLES

Experimental Procedures

Experiments were performed using animal hearts to compare the effectiveness of the imaging using NADH recording of the present disclosure compared to Triphenyltetrazolium chloride (TTC) staining. As will be described in more detail below, the imaging using NADH recording performed as good as TTC staining. Importantly, it was done in living tissue, did not require any additional processing time or the use of a dye to achieve the same performance.

Animal Procedures

Ex-vivo experiments were conducted using excised blood-free hearts of a rat (200-300 g Sprague-Dawley, n=8) and rabbit (2.5-3.5 Kg New Zealand White, n=3). The animals were heparinized and anesthetized using standard procedures. Hearts were then excised, the aorta was cannulated and Langendorff-perfused at constant pressure (50 mmHg) with oxygenated, buffered Tyrode solution at room temperature. The hearts were placed on top of a grounding pad and submerged in 37° C. Tyrode solution during ablation.

In situ experiments (n=3) were performed using anesthetized open-chest rats (200-300 g Sprague-Dawley). After an IP injection of Telazol (40 mg/kg) the hair on the chest and back were shaved, the animal was immobilized on a heated platform, and an ablation pad was placed beneath the animal. Immediately after opening chest cavity, the ablations were carried out as the exposed epicardial surface was imaged. All anesthesia and euthanasia procedures were in compliance with the institutional Animal Care and Use committee approved protocols.

Ablation Protocols and NADH Recordings

Radiofrequency energy was delivered using a non-cooled blazer catheter with a 4 mm tip (EP Technologies, Boston Scientific Corporation). Tip temperatures ranged between 50 to 70° C. The catheter was placed perpendicular to the epicardial surface. Ablation durations varied from 15 to 60 sec with a maximum power of 50 W. The epicardial surface was illuminated with UV light (350/25 nm) using a 100 Watt mercury lamp (Zeiss HBO100 W/2). To record the epicardial fluorescence of NADH, the emitted light was filtered (460/25 nm) and imaged using a CCD camera (Andor Ixon DV860) that has high quantum efficiency for wavelengths corresponding to NADH fluorescence (80% QE at 460 nm).

Optical Mapping Experiments

Hearts were stained with the potentiometric dye RH237 (Molecular Probes, 10 μM solution) and Blebbistatin was added to the perfusate (10 μM final concentration) to reduce motion artifact. A dual optical mapping system comprised of two CCD cameras (Andor IXON DV860s) fitted with a dual port adapter (Andor CSU Adapter Dual Cam) and a dichroic mirror (610 nm) was used to image the epicardial fluorescence of RH237 (250-500 fps) and NADH (2 fps) from the same field of view. To record optical action potentials, the epicardium was illuminated using two light emitting diodes (LumiLEDs, 530/35 nm). The resulting fluorescence of RH237 was long-pass filtered at 680 nm. NADH fluorescence was recorded with the other CCD camera as described above.

The fluorescence of RH237 was processed to subtract background fluorescence from each image and signals for each pixel were normalized. RH237 fluorescence signals were smoothed using a median temporal filter (3 sample width). Isochronal maps of activation times were generated to show wave front propagation. The average amplitude of optical action potentials at each pixel was computed to reveal spatial changes in the amount of electrically active tissue.

TTC Staining

Triphenyltetrazolium chloride (TTC) vital staining is a standard procedure for assessing acute necrosis. Immediately after the imaging protocol was completed, the tissue was retrogradely perfused through the coronaries with a 1.0% TTC in Tyrode solution. The heart was then submersed in the TTC solution for an additional 8 min. Metabolically active tissue appeared crimson. Necrotic tissue appeared white.

Experimental Results

FIG. 4A, FIG. 4B, FIG. 4C, FIG. 4D and FIG. 4E illustrate RF ablation lesions in blood-free excised rat hearts. The first set of experiments was conducted in excised hearts from healthy rats of either sex. Hearts were retrograde-perfused with Tyrode solution. The epicardium of 8 hearts was ablated and imaged. Two ablation lesions were placed next to each other on 4 of the hearts. An example of an RF ablation probe in the position to deliver a lesion onto the epicardial surface is illustrated in FIG. 4A, and the visual appearance of a typical lesion after a standard RFA ablation protocol is illustrated in FIG. 4B. As illustrated in FIG. 4B, ablations caused immediate changes in the visual appearance of the epicardial surface as a distinct area of pale tissue. The paleness corresponds to denaturation of myoglobin at temperatures above 60° C. The heart was then placed on a constant pressure perfusion system and imaged using either a single or dual CCD camera system. FIG. 4C illustrates the appearance of two distinct RF ablation lesions, as revealed by fNADH imaging, where partially ischemic tissue appears as blotchy white. As illustrated in FIG. 4C, fNADH images revealed that the areas of ablation appeared markedly dark when compared to the surrounding unablated myocardium.

After imaging, the hearts were stained with vital dye TTC, which is illustrated in FIG. 4D, and sliced transmurally to examine the ablation lesions, which is illustrated in FIG. 4E. As illustrated in FIG. 4D after TTC staining, metabolically active tissue appears red and irreversibly damaged tissue appears white. FIG. 4E illustrates transverse slicing through the heart to show the depth of two lesions placed on opposite epicardial surfaces using two different power settings.

Spatial Extent and Temporal Stability of RF Ablation Lesions.

Figure 5A:
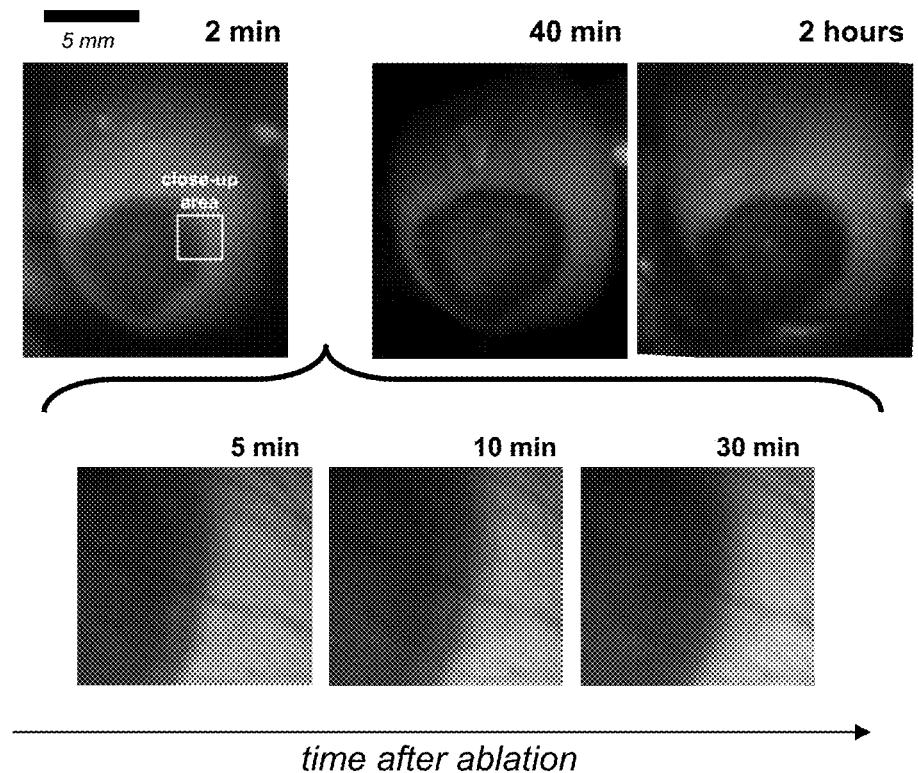
FIG. 5A illustrates lesion stability over time as seen on fNADH-sensitive channel.
Figure 5B:
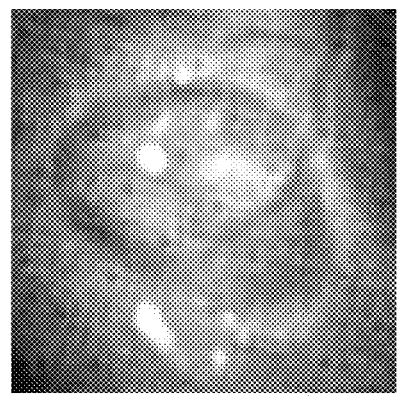
FIG. 5B illustrates an image of radiofrequency ablation lesion on the epicardial surface of an excised rat heart 2 months after survival surgery as seen on fNADH-sensitive channel.

FIG. 5A and FIG. 5B illustrate lesion stability over time. Specifically, the top row shows snapshots of fNADH at different time points (2-120 minutes) after RF ablation. The white box on the top left image indicates close-up area used in the three lower snapshots, which illustrate a close-up of the lesion border over three intermediate time points (5, 10 and 30 mins).

As shown in FIG. 5A and FIG. 5B, fNADH levels in ablated tissue did not return to their pre-ablation values and the size of the lesions did not significantly change over the course of the experiments (approx. 2 hours). As illustrated by the three lower close-up snapshots in FIG. 5A and FIG. 5B, areas in the fNADH images that corresponded to the lesions became homogenously dark over time.

Figure 6A:
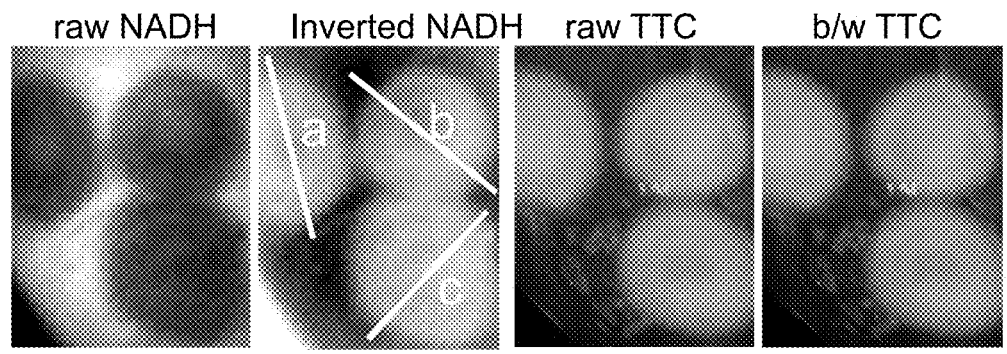
FIG. 6A, FIG. 6B and FIG. 6C illustrate comparison between the sizes of the RF lesions as they are seen on fNADH-sensitive channel and after TTC staining.
Figure 6B:
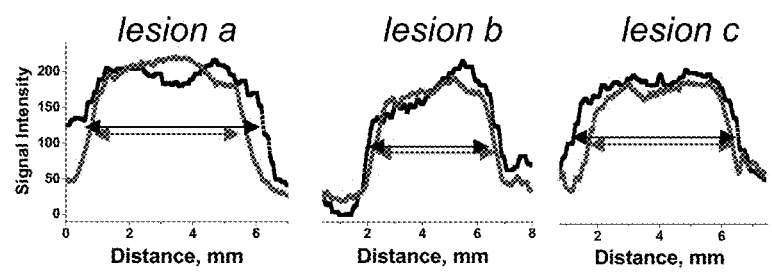
Figure 6C:
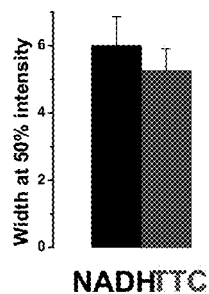

As illustrated in FIG. 6A, FIG. 6B and FIG. 6C, the size of the lesions measured from the fNADH images was identical to the size of the areas that stained negative for TTC. Specifically, FIGS. 6A and 6B illustrate sizes of the RF lesions as seen on fNADH-sensitive channel and after TTC staining. In FIG. 6A snapshots of the three lesions on the surface of the rabbit heart respectively illustrate the raw NADH image, inverted NADH image (i.e., the LUT scale of raw fNADH images was inverted to show lesions in white), raw TTC image and black and white TTC image (i.e., gray scale). The three graphs of FIG. 6B respectively correspond to the intensity profile through each lesion a, b, and c identified in the snapshots of FIG. 6A. As illustrated by the bar graph of FIG. 6C, widths of the lesions were not significantly different when examined using fNADH and TTC staining.

TTC staining is a common method to determine tissue viability. It relies on the ability of dehydrogenase enzymes and NADH to react with tetrazolium salts to form a formazan pigment. Since both methods rely on the presence of active NADH, the measurement of lesion size is similar for the two methods. Thus, as illustrated by the graphs in FIG. 6B, live imaging of NADH fluorescence provides an estimate of the area of TTC-positive tissue with better than 95% accuracy. From a clinical perspective, the stability of RF ablation lesions as seen in fNADH images suggests that UV-based imaging of NADH can be acquired after multiple RF ablations have been performed, since lesion appearance remains stable for several hours.

Identifying Functional Gaps Between RF Ablation Lesions

Figure 7A:
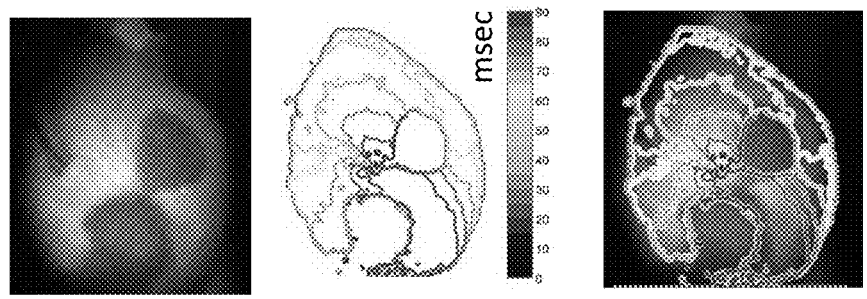
FIG. 7A, FIG. 7B and FIG. 7C illustrate occurrence of reentry between two RF lesions based on data from dual imaging of epicardial electrical activity using voltage sensitive dye and fNADH. Reentry formation occurs as electrical waves propagate through narrow isthmus between two RF lesions.
Figure 7B:
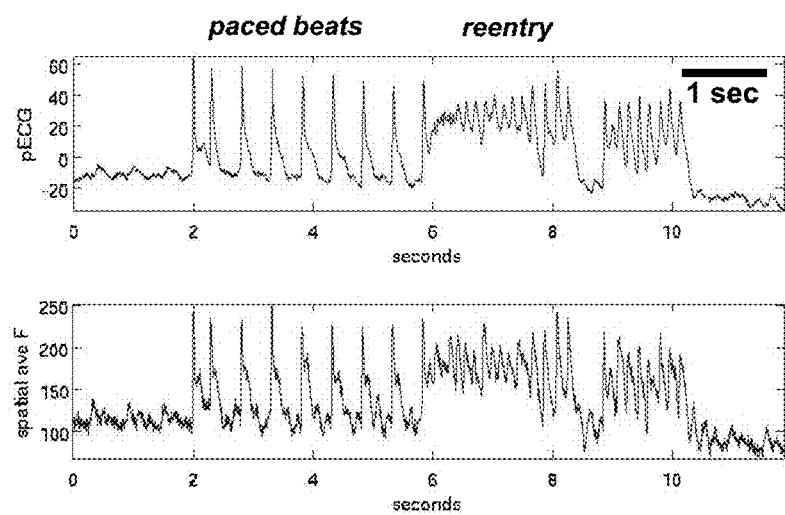
Figure 7C:
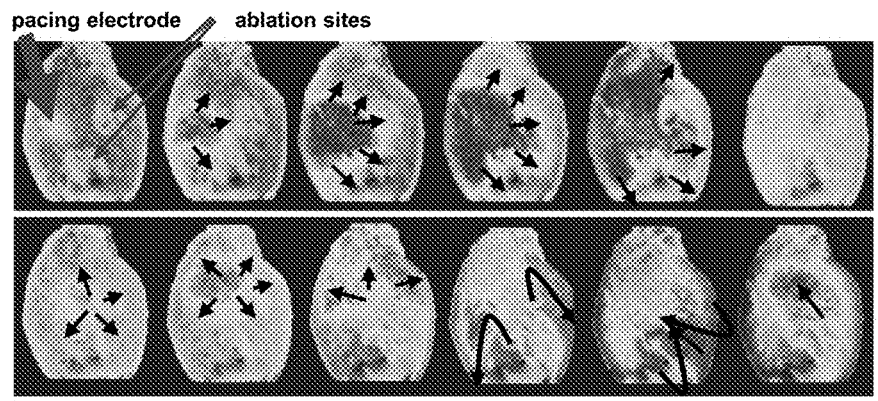

FIG. 7A, FIG. 7B, and FIG. 7C illustrate dual imaging of epicardial electrical activity and fNADH of the propagation through narrow isthmus between two RF lesions. As discussed above, incomplete lesions may be even more dangerous if they serve as anatomical routes for reentry and inter-lesion isthmuses as small as 1 mm can lead to recurrent conduction. To study propagation through inter-lesion isthmuses wavefronts of activity between two closely placed RF lesions were analyzed. A bipolar pacing electrode was placed on the epicardium above the lesions and current was applied at twice the diastolic threshold (2.5 mA). Paced waves caused spontaneous reentrant circuits around the lesions when a functional isthmus was present. An example of this activity is illustrated in the sequential snapshots of FIG. 7C. The three snapshots in FIG. 7A respectively illustrate an fNADH image of tissue with two lesions, an isochronal map of electrical activity of one of the reentrant circuits recorded using the voltage-sensitive dye RH237, and the superposition of the isochronal map on the FNADH image. FIG. 7B illustrates the pseudo ECG trace reconstructed by averaging optical action potentials from all pixels in individual frame, which corresponds to the sequence shown in FIG. 7C. FIG. 7C illustrates sequential snapshots of processed RH237 sequence that illustrate propagation of paced beats and reentry around the lesions.

To create the isochronal maps and to reveal propagating wave fronts (as illustrated in FIG. 7A, FIG. 7B and FIG. 7C), optical action potentials were normalized to show propagating wave fronts in an all-or-none fashion. This is useful for illustrating propagation but it can be misleading because it obscures the true optical action potential amplitudes. To better represent true optical action potential amplitudes, the RH237 signal at each pixel was scaled as a percentage of the maximum optical action potential amplitude for all the pixels.

FIG. 8A, FIG. 8B, FIG. 8C and FIG. 8D illustrate fNADH and electrical activity across the isthmus between two RF lesions. Specifically, FIG. 8A illustrates an x-t representation of the amplitudes of five sequential action potentials along the black line in the adjacent RH237 image. In FIG. 8A the x-axis is the distance between the two lesions and the y-axis represents time with action potentials indicated by asterisks on the right. FIG. 8B illustrates the graph overlaid on the interlesion intensity profile for fNADH with the profile of the action potential amplitude. The two profiles had a correlation coefficient of r=0.95, P<0.05. The inter-lesion profile of the optical action potential amplitude is illustrated in FIG. 8C as an x-t plot for six sequential beats, with the x-axis being the distance between the centers of the two lesions. In FIG. 8D the gap is identified by fNADH which gives it a light appearance whereas the ablated lesion is identified by lack of fluorescence which gives the tissue a dark appearance. The interlesion profile of action potential amplitude was then compared to the interlesion profile of fNADH intensity. The two were highly correlated (r=0.95). These findings suggest that fNADH loss can serve as a direct marker for the diminished functional state of the tissue near the ablation site.

Lack of fNADH Indicates Muscle Damage and Not Damage to Major Coronary Vessels

Abundant mitochondria that contain NADH make cardiac myocytes particularly suitable for fNADH imaging. Reduced fNADH at the site of the RF ablation lesions indicates loss of myocyte membrane integrity, as cell and mitochondrial membranes are rapidly damaged by thermal stress. Notably, cardiac muscle cell necrosis within the ablation site does not necessarily mean that the integrity of all underlying structures, such as coronary vessels, was destroyed. In the experiments a disruption of major coronary vessel structure was not observed. This is because, if vessels were disrupted, then tissue downstream of damaged vessels would become ischemic, causing fNADH to increase. Yet, as illustrated in FIG. 6A, fNADH levels near the lesions did not significantly change before and after ablation. The patches of whiter tissue occasionally seen near the ablation site occurred prior to the RF ablation event, potentially as a result of transient low perfusion that temporarily caused local ischemia. Other evidence of intact coronary structure was the homogeneity of post-ablation TTC staining: any major vessel damage would have been indicated as areas of unstained tissue outside the RF ablation lesion. However, all of the 13 RF ablation lesions made during the experiment and identified with TTC were localized strictly to the RF lesion site. Finally, as illustrated in FIG. 4B, observation of intact vessels on the epicardial surface did not indicate severe damage to major vessels at the ablation sites.

Conductive vs. Direct Resistive Heating

Figure 9D:
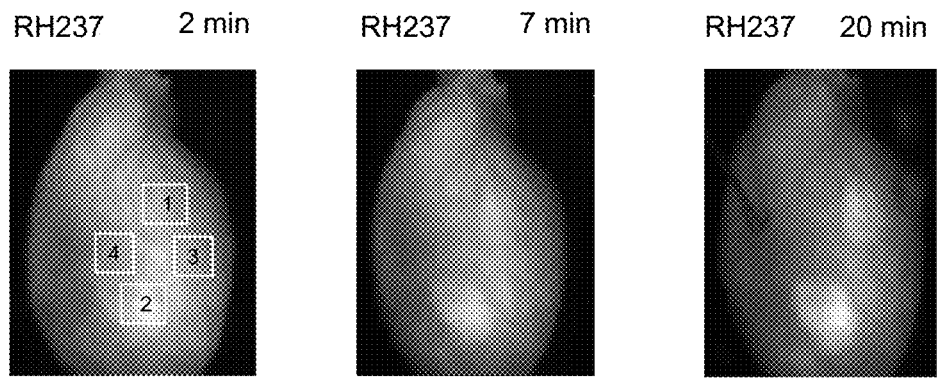
Figure 9D:
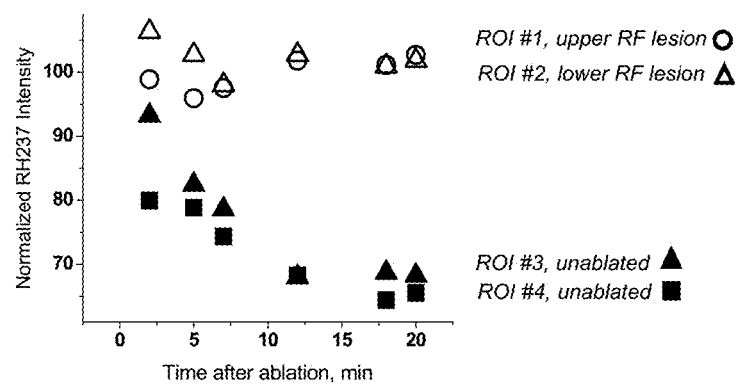

FIG. 9A, FIG. 9B, FIG. 9C and FIG. 9D illustrate RH237 retention within the ablation area. Specifically, FIGS. 9A-9C illustrate three sequential snapshots of rat heart bolus stained with RH237. As illustrated in FIGS. 9A-9C, RH237 fluorescence decreases over time, highlighting the lesions as areas that retain the dye. FIG. 9D illustrates the intensity of RH237 staining acquired from the four regions of interest (ROI) identified in FIG. 9A. The solid points, which trend downward over time, correspond to ROIs in unablated areas, and the open points, which remain stable over time, correspond to ROIs in the lesion area.

Figure 10A:
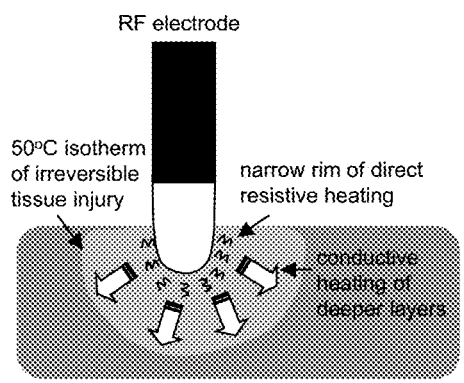
FIG. 10A, FIG. 10B, FIG. 10C and FIG. 10D illustrate RH237 retention after RF ablation procedure as it compares to NADH fluorescence.
Figure 10B:
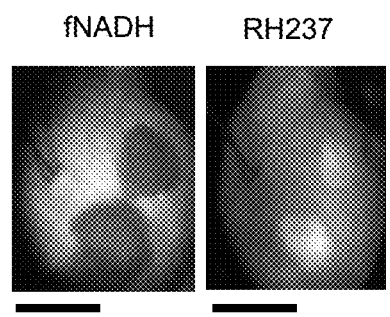
Figure 10C:
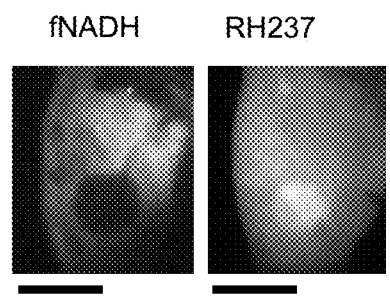
Figure 10D:
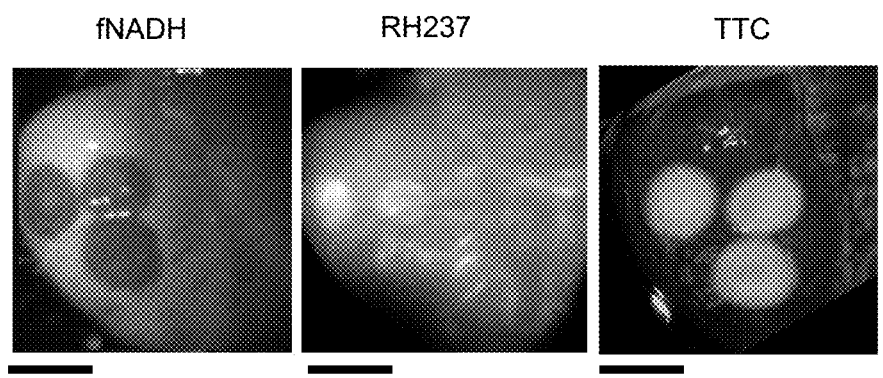

As illustrated in FIG. 10A, FIG. 10B, FIG. 10C and FIG. 10D, during optical mapping the washout rate of RH237 was less within the ablation lesions than in the normal tissue, which resulted in high contrast between the lesions and normal tissue in the raw RH237 images. FIG. 10A, FIG. 10B, FIG. 10C and FIG. 10D illustrate RH237 retention after RF ablation procedure compared to NADH fluorescence and visual appearance of the epicardium. FIG. 10A is a schematic representation of lesion formation by RF catheter. FIGS. 10B and 10C illustrate two different rat hearts showing a lesion in an fNADH image (the left-hand side image) and the corresponding RH237 image (the right-hand side image). The scale bars below these images correspond to 5 mm. FIG. 10D illustrates a rabbit heart with three RF ablations as it appears within fNADH, RH237 images and TTC staining images, with the scale bars below these images corresponding to 5 mm. It should be noted that a brownish rim within white TTC channel coincides with RH237 retention area. Importantly, as can be seen by a comparison of the fNADH and RH237 images in FIG. 10B and FIG. 10C, the diameter of the bright areas of RH237 (corresponding to a lesion) was significantly smaller than the area of the lesion indicated by fNADH. Lesion size in RH237 images corresponded to the internal ring-like structure often seen on both fNADH and TTC images, such as those illustrated in FIG. 6A.

The most plausible explanation for the bright RH237 areas is the acute damage to epicardial capillaries that occurs at the site of direct resistive heating immediately beneath the RF electrode. This then reduces washout of the RH237 dye, as can be seen in FIGS. 10B and 10C. RF current heats tissue through resistive heating of a narrow rim of tissue that is in direct contact with the ablation electrode. Deeper tissue heating is a result of passive heat conduction from this small annular volume. Temperatures above 50° C. are required for irreversible myocardial injury; at temperatures above 100° C., boiling occurs at the electrode-tissue contact, forming a coagulum (i.e., the brown rings in FIG. 6A). Direct comparison between two modes of imaging the lesions (fNADH and RH237) may allow direct resistive heating to be distinguished from conductive heat transfer to deeper tissue layers.

RF Lesions in Blood Perfused Rat Hearts

Figure 11A:
FIGS. 11A-11D illustrate visualization of RF ablation lesions in blood-perfused open-chest animals.
Figure 11B:
Figure 11C:
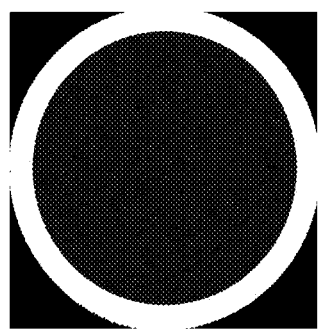
Figure 11D:
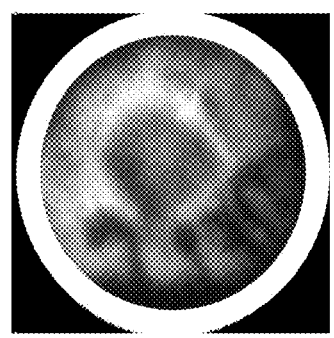

FIG. 11A, FIG. 11B, FIG. 11C and FIG. 11 illustrate a visualization of RF ablation lesions in blood-perfused open-chest animals. Specifically, FIG. 11A is an open chest brightfield image of a rat heart with epicardial RF ablation lesion, and FIG. 11B illustrates the same heart as observed using fNADH. As illustrated in FIG. 11C, submerging the above ablated heart in externally added blood completely obscured fNADH signals. Blood is an optically dense medium and, within the visible light band, it interferes with spectroscopic assessment of tissue properties. Therefore, a critical issue was to show the feasibility of fNADH-based imaging in blood perfused animals. This was done by placing lesions on the epicardium immediately after opening the animal's chest and acquiring fNADH images in the same way as the excised heart experiments. As illustrated in FIG. 11B, major blood vessels appeared as dark tracks within these images, but the RF ablation lesion was clearly revealed, which indicated that mitochodria-rich cardiac muscle provides enough fNADH to reveal surrounding unablated tissue. As illustrated in FIG. 11C, the entire field became dark when the epicardial surface of the same heart was submerged in blood. As illustrated in FIG. 11D, RF ablation lesions were revealed within the fNADH images when blood was displaced from the epicardial surface using a sheet of transparent polyvinylidene chloride.

Figure 12:
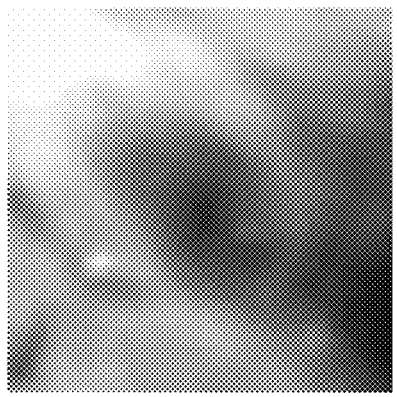
FIG. 12 is an image of an ablation lesion on the endocardial surface of blood perfused canine left atrial tissue near pulmonary veins.

FIG. 12 illustrates an ablation lesion obtained from the left atrial tissue of a canine at the time of open heart surgery. The tissue is located near the area of atrial fibrillation pulmonary vein isolation procedures. The left atrium was opened surgically and the blood had been removed from the field. The animal was in bypass at the time to allow for normal perfusion of the atrial tissue.

Figure 13:
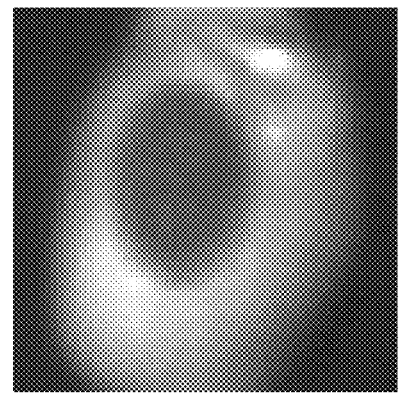
FIG. 13 is an image of an ablation lesion on epicardial surface of blood-free rat hart after cryo-ablation.

FIG. 13 is an image of an ablation lesion on epicardial surface of rat hart after cryo-ablation. This image was obtained from a blood-free excised rat heart. Cryoablation was done using liquid nitrogen on a the tip of a metal tip catheter.

Figure 14:
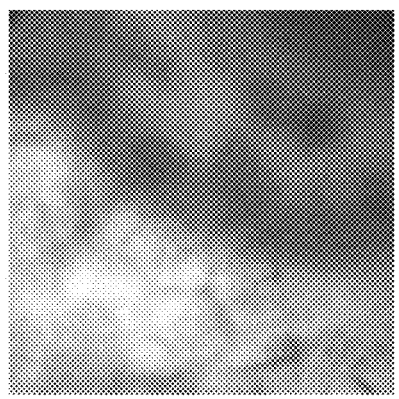
FIG. 14 illustrates fNADH lesion in rat blood-perfused liver that has been acutely ablated using radiofrequency ablation.

FIG. 14 illustrates liver perfused rat tissue that has been acutely ablated using radiofrequency ablation. This was done to illustrate how ablation lesions look on the surface of other organs.

Figure 15:
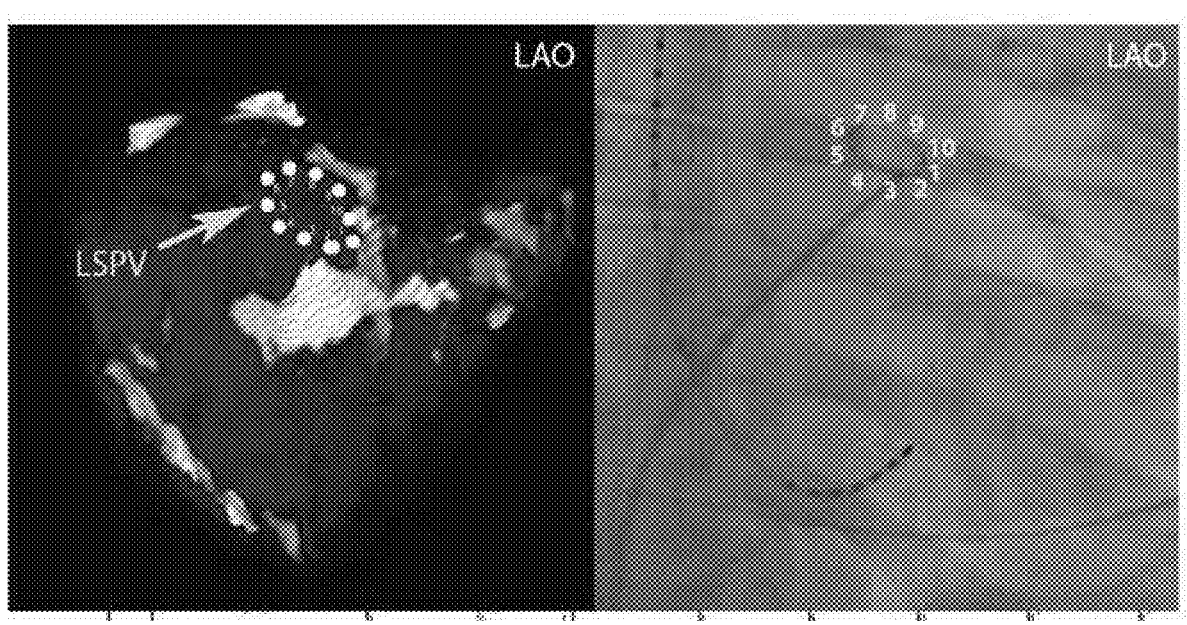
FIG. 15 is a 2D image on the right of a standard catheter and reconstruction into 3D integrated into 3D mapping system. A computer system and program can be used to convert the acquired 2D image of NADH fluorescence into a 3D image superimposed on the atrial anatomy as displayed.

FIG. 15 is a 2D image on the right of a standard catheter and reconstruction into 3D integrated into 3D mapping system. A computer system and program can be used to convert the acquired 2D image of NADH fluorescence into a 3D image superimposed on the atrial anatomy as displayed.

In some embodiments, a method for acquiring a real time image of ablated endocardial heart muscle tissue and unablated gaps at the pulmonary vein and left atrial junction is provided, comprising inflating an inflatable compliant balloon with transparent fluid for displacing surrounding blood to allow visualization of NADH fluorescence; illuminating with an ultra-violet light for exciting mitochondrial NADH of the pulmonary vein and left atrial tissue using UV capable fiber; detecting NADH fluorescence from the illuminated pulmonary vein and left atrial tissue using optical imaging bundle; creating a fluorescence image with a fluorescence camera by filtering the detected NADH fluorescence with 460 nm band-pass filter; wherein the detected fluorescence image shows the physiology of the ablated lesion having a dark appearance due to lack of fluorescence, gaps having a light appearance due to normal fluorescence, and any ischemic or injured tissue having a brighter halo type appearance surrounding the ablated lesion.

In some embodiments, a method for acquiring a real time image of ablated endocardial heart muscle tissue and unablated gaps at the pulmonary vein and left atrial junction is provided, comprising inflating an inflatable compliant balloon with transparent fluid for displacing surrounding blood to allow visualization of NADH fluorescence; illuminating with ultra-violet light for exciting mitochondrial NADH of the pulmonary vein and left atrial tissue using uv capable fiber; detecting NADH fluorescence from the illuminated pulmonary vein and left atrial tissue using a CMOS camera; creating a fluorescence image with a fluorescence camera by filtering the detected NADH fluorescence with 460 nm band-pass filter; wherein the detected fluorescence image shows the physiology of the ablated lesion having a dark appearance due to lack of fluorescence, gaps having a light appearance due to normal fluorescence, and any ischemic or injured tissue having a brighter halo type appearance surrounding the ablated lesion.

In some embodiments, a method of producing visualizations of ablated lesions in the pulmonary vein area and provide additional information about physiology is provided, the method comprising the steps of illuminating, using an ultraviolet light source, tissue that includes ablated tissue and unablated tissue around the ablated tissue; imaging the illuminated tissue; and producing a display of the imaged, illuminated tissue, wherein the display illustrates the ablated tissue as having less fluorescence than the unablated area around the ablated tissue. In some embodiments, the display may illustrate areas of high fluorescence surrounded by an area of lower fluorescence or lack of fluorescence. In some embodiments, the illustrated areas of high fluorescence surrounded by the area of lower fluorescence indicate that the areas of high fluorescence are not ablated. In some embodiments, the fluorescence is caused by NADH in the illuminated tissue. In some embodiments, the illumination, imaging and producing are performed while a radio frequency, cryoablation or laser catheter is used to ablate the tissue. In some embodiments, the illumination and imaging are performed using a fiber optic waveguide coupled to a tip of the lumen catheter, the fiber optic waveguide delivers ultraviolet light from the ultraviolet light source to the illuminated tissue. In some embodiments, the tissue is heart tissue. In some embodiments, the imaging of the illuminated tissue is performed without addition of chemicals to the illuminated tissue.

In some embodiments, a method of treating Atrial Fibrillation (AF) is provided, the method comprising the steps of ablating a portion of the atrial tissue; illuminating tissue using an ultraviolet light source; imaging the illuminated tissue using fluorescence camera and a filter for allowing visualization of fluorescence; producing a display of the imaged illuminated tissue; identifying gaps between ablated tissue based on the display of the imaged illuminated tissue; wherein ablated tissue is identified by lack of fluorescence which gives the tissue a dark appearance and wherein gaps constituting unablated tissue are identified by fluorescence which gives them a light appearance and ablating the identified unablated tissue gaps between ablated tissue. In some embodiments, the display illustrates the ablated tissue as having less fluorescence than the gaps.

In some embodiments, a system for imaging tissue includes a catheter having a distal end and a proximal end; an inflatable balloon disposed about the distal end of the catheter; and an optical housing extending from the distal end of the catheter into the balloon, the optical housing being configured to position inside the balloon a light source for illuminating a tissue outside the balloon and a camera for imaging the illuminated tissue.

In some embodiments, a system for imaging tissue includes a catheter having a distal end and a proximal end; an inflatable balloon disposed about the distal end of the catheter; and an optical housing extending from the distal end of the catheter into the balloon; a light source inside the balloon, the light source being supported by the optical housing and configured to excite native reduced form of nicotinamide adenine dinucleotide or nicotinamide adenine dinucleotide hydrogen (NADH) in a tissue; and a camera inside the balloon, the camera being supported by the optical housing and configured to image the tissue illuminated by the light source.

In some embodiments, a system for imaging tissue includes a catheter having a distal end and a proximal end; an irrigation port to displace blood with a fluid about the distal end of the catheter; and an optical housing extending from the distal end of the catheter, the optical housing being configured to support a light emitting diode light source for illuminating tissue and a visualization device including a plurality of image sensors that convert an optical image into an electronic signal for imaging the illuminated tissue.

In some embodiments, a system for imaging tissue includes a sheath for infusing a fluid capable of displacing blood and transmitting light; a catheter disposed within the sheath, the catheter having a distal end and a proximal end; an optical housing extending from the distal end of the catheter, the optical housing being configured to support a light emitting diode light source for illuminating tissue and a visualization device including a plurality of image sensors that converts an optical image into an electronic signal for imaging the illuminated tissue.

In some embodiments, a method for imaging tissue includes advancing to a tissue a catheter comprising an inflatable balloon disposed about the distal end of the catheter and an optical housing extending from the distal end of the catheter into the balloon to position a light source and a camera inside the balloon; ablating the tissue; illuminating with the light source an area of tissue including tissue treated by ablation and surrounding tissue to excite NADH in the area of tissue; imaging with an imaging device the area of tissue to detect NADH fluorescence of the area of tissue; and producing a display of the imaged, illuminated tissue, the display illustrating ablated tissue as having less fluorescence than non-ablated tissue.

The foregoing disclosure has been set forth merely to illustrate various non-limiting embodiments of the present disclosure and is not intended to be limiting. Since modifications of the disclosed embodiments incorporating the spirit and substance of the disclosure may occur to persons skilled in the art, the presently disclosed embodiments should be construed to include everything within the scope of the appended claims and equivalents thereof.

What is claimed is:

1. A system for imaging tissue, the system being configured for use in connection with tissue ablation, comprising:
a light source providing light for illuminating a tissue having at least one wavelength sufficient to excite mitochondrial nicotinamide adenine dinucleotide hydrogen (NADH) in the tissue;
a sensor for detecting NADH fluorescence from the illuminated tissue, the sensor being configured to receive light having at least one wavelength to detect the NADH fluorescence from the illuminated tissue; and
a processor programmed to perform the steps of:
obtaining the detected NADH fluorescence from the sensor during ablation of the tissue,
generating a digital representation of the detected NADH fluorescence for monitoring a progression of the ablation of the tissue, and
while the tissue is being ablated, determining a decrease in the detected NADH fluorescence and updating the digital representation to show the measured decrease in the detected NADH fluorescence that is indicative of the progression of the ablation of the tissue to enable a user to determine the need for further ablation while the tissue is being ablated.

2. The system of claim 1, wherein the light for illuminating the tissue has at least one wavelength between about 300 nm and 400 nm.

3. The system of claim 1, wherein the sensor is configured to receive light having at least one wavelength between about 435 nm and about 485 nm.

4. The system of claim 1, further comprising an ablation device, the ablation device having an energy source selected from the group consisting of radiofrequency energy, microwave energy, electrical energy, electromagnetic energy, cryoenergy, laser energy, ultrasound energy, acoustic energy, chemical energy, and thermal energy.

5. The system of claim 4, further comprising an elongate body, and wherein the ablation device is disposed at a distal end of the elongate body.

6. The system of claim 5, further comprising an irrigation port configured to deliver a fluid to the distal end of the elongate body.

7. The system of claim 1, wherein the tissue is one of skeletal muscle, liver tissue, kidney tissue, and cardiac tissue.

8. The system of claim 1, further comprising one or more optical fibers to deliver the light from the light source to the tissue and to deliver the NADH fluorescence to the sensor.

9. A system for imaging tissue comprising:
an ablation device for ablating a tissue;
a light source providing light for illuminating the tissue to excite mitochondrial nicotinamide adenine dinucleotide hydrogen (NADH) in the tissue, wherein the light from the light source has at least one wavelength between about 300 nm and about 400 nm sufficient for NADH excitation;
a sensor being configured to receive light to detect NADH fluorescence from the illuminated tissue; and a processor programmed to perform the steps of:
- obtaining the detected NADH fluorescence from the sensor during ablation of the tissue using the ablation device,
- generating a digital representation of the detected NADH fluorescence for monitoring a progression of the ablation of the tissue, wherein a decrease in the detected NADH fluorescence from the illuminated tissue is indicative of the progression of the ablation of the tissue to enable a user to determine the need for further ablation, and
- while the tissue is being ablated, determining a decrease in the detected NADH fluorescence and updating the digital representation to show the measured decrease in the detected NADH fluorescence throughout the ablation of the tissue.

10. The system of claim 9, further comprising an elongate body, the elongate body having the ablation device and an inflatable balloon disposed about a distal end of the elongate body.

11. The system of claim 9, wherein the ablation device has an energy source selected from the group consisting of radiofrequency energy, microwave energy, electrical energy, electromagnetic energy, cryoenergy, laser energy, ultrasound energy, acoustic energy, chemical energy, and thermal energy.

12. The system of claim 9, wherein the light source is a UV light emitting diode (LED).

13. The system of claim 9, wherein the sensor is configured to convert an optical image into an electronic signal.

14. The system of claim 9, further comprising one or more optical fibers to deliver the light from the light source to the tissue and to deliver the NADH fluorescence to the sensor.

15. The system of claim 9, further comprising a first light source and a second light source capable of generating light of a different wavelength than the first light source.

16. The system of claim 9, wherein the tissue is one of skeletal muscle, liver tissue, kidney tissue, or cardiac tissue.

17. A method for imaging tissue comprising:
- obtaining detected NADH fluorescence from a sensor during ablation of a tissue using an ablation device,
- generating a digital representation of the detected NADH fluorescence for monitoring a progression of the ablation of the tissue, wherein a decrease in the detected NADH fluorescence from the illuminated tissue is indicative of the progression of the ablation of the tissue, and
- while the tissue is being ablated, determining a decrease in the detected NADH fluorescence and updating the digital representation to show the measured decrease in the detected NADH fluorescence that is indicative of the progression of the ablation of the tissue to enable a user to determine the need for further ablation.

18. The method of claim 17, further one or more optical fibers are employed to deliver the light from the light source to the tissue and to deliver the NADH fluorescence to the sensor.

19. The method of claim 17, wherein the ablating is performed with radiofrequency energy, microwave energy, electrical energy, electromagnetic energy, cryoenergy, laser energy, ultrasound energy, acoustic energy, chemical energy, and thermal energy.

20. The method of claim 17, wherein the tissue is one of skeletal muscle, liver tissue, kidney tissue, or cardiac tissue.

* * * * *